United States Patent
Krizman et al.

(10) Patent No.: US 8,293,485 B2
(45) Date of Patent: *Oct. 23, 2012

(54) MULTIPLEX LIQUID TISSUE™ METHOD FOR INCREASED PROTEOMIC COVERAGE FROM HISTOPATHOLOGICALLY PROCESSED BIOLOGICAL SAMPLES, TISSUES AND CELLS

(75) Inventors: David B. Krizman, Gaithersburg, MD (US); Marlene M. Darfler, Derwood, MD (US)

(73) Assignee: Expression Pathology, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/048,522

(22) Filed: Mar. 15, 2011

(65) Prior Publication Data
US 2011/0229917 A1 Sep. 22, 2011

Related U.S. Application Data

(63) Continuation of application No. 11/915,582, filed as application No. PCT/US2006/020166 on May 25, 2006, now Pat. No. 7,906,301.

(60) Provisional application No. 60/684,167, filed on May 25, 2005.

(51) Int. Cl.
G01N 33/53 (2006.01)
(52) U.S. Cl. .......................................... 435/7.1; 436/518
(58) Field of Classification Search .................. None
See application file for complete search history.

(56) References Cited

U.S. PATENT DOCUMENTS

| | | | |
|---|---|---|---|
| 5,356,637 | A | 10/1994 | Loosen et al. |
| 5,672,696 | A * | 9/1997 | Wang et al. ............... 536/25.42 |
| 5,985,337 | A | 11/1999 | Blortz et al. |
| 7,473,532 | B2 | 1/2009 | Darfler et al. |
| 7,501,286 | B2 | 3/2009 | Gygi |
| 2002/0090620 | A1* | 7/2002 | Davis et al. ............... 435/6 |
| 2002/0182647 | A1 | 12/2002 | Emmert-Buck |
| 2004/0096907 | A1 | 5/2004 | Bohrmann et al. |
| 2005/0069911 | A1 | 3/2005 | Lee et al. |
| 2005/0095634 | A1 | 5/2005 | Baker et al. |
| 2008/0108795 | A1 | 5/2008 | Guo |

FOREIGN PATENT DOCUMENTS

| | | |
|---|---|---|
| JP | 2004-157124 A | 6/2004 |
| WO | WO 2005/040396 | 6/2005 |
| WO | WO 2005/080579 | 9/2005 |

OTHER PUBLICATIONS

Banerjee et al. *Biotechniques* 18:768-71, 1995.
Bons et al. Protein profiling as diagnostic tool in clinical chemistry: a review. *Clin. Chem. Lab. Med.* 43(12):1281-90, 2005. [0058].
Espina et al. Protein microarrays: molecular profiling technologies for clinical specimens. *Proteomics* 3(11):2091-100, 2003. [0058].
Ikeda et al. Extraction and analysis of diagnostically useful proteins from formalin fixed, paraffin-embedded tissue sections. *J. Histochem. Cytochem.* 46(3):397-403, 1998. [0058].
Loor et al. Evaluation of a human pancreas-specific antigen by enzyme-linked immunosorbent assay. *Clin. Chim. Acta.* 117(3):251-8, 1981. [0058].
Posadas et al. Proteomic analysis for the early detection and rational treatment of cancer—realistic hope? *Annals of Oncology* 16(1):16-22, Jan. 2005.
Shi et al. Antigen retrieval techniques: current perspectives. *J. Histochem. Cytochem.* 49(8):931-73, 2001. [0058].
Stemmann et al. Dual inhibition of sister chromatid separation at metaphase. *Cell* 107:715-726, 2001. [0062].
Ballif et al, "Quantitative phosphorylation profiling of the ERK/p90 ribosomal S6 kinase-signaling cassette and its targets, the tuberous sclerosis tumor suppressors." *PNAS* 102(3):667-672, Jan. 18, 2005.
Bagnato, et al. "Proteomics Analysis of Human Coronary Atherosclerotic Plaque: A Feasibility Study of Direct Tissue Proteomics by Liquid Chromatography and Tandem Mass Spectometry." *Molecular & Cellular Proteomics* 6:1088-1102, Jun. 1, 2007.
Erba, "Systematic analysis of the epidermal growth factor receptor by mass spectrometry reveals stimulation-dependent multisite phosphorylation." *Mol Cell Proteomics* 4(8):1107-21, Aug. 2005.
Gerber et al, "Absolute quantification of proteins and phosphoproteins from cell lysates by tandem MS." *PNAS* 100(12):6940-6945, Jun. 10, 2003.
Guzel, et al. "Multiple Reaction Monitoring Assay for Pre-eclampsia Related Calcyclin Peptides in Formalin Fixed Paraffin Embedded Placenta." *J. Proteome Res.* 10(7):3274-3282, 2011.
Hawridge, et al. "Quantitative mass spectral evidence for the absence of circulating brain natriuretic peptide (BNP-32) in severe human heart failure." *PNAS* 102(48):17442-17447, Nov. 29, 2005.
Prieto, "Liquid Tissue: proteomic profiling of formalin-fixed tissues." *Bio Techniques* 38:S32-S35, Jun. 2005. Williamson, et al. "Automated Identification and Quantification of Protein Phosphorylation Sites by LC/MS on a Hybrid Triple Quadruple Linear Ion Trap Mass Spectrometer." *Molecular & Cellular Proteomics* 5:337-346, Feb. 1, 2006.
Prosecution History of U.S. Appl. No. 12/348,868.
Prosecution History of U.S. Appl. No. 11/915,581.
Prosecution History of EP Application 04719188.7.
Prosecution History of EP Application 06771123.4.

\* cited by examiner

*Primary Examiner* — Jacob Cheu
(74) *Attorney, Agent, or Firm* — Perkins Coie LLP

(57) ABSTRACT

The invention provides methods for multiplex analysis of biological samples of formalin-fixed tissue samples. The invention provides for a method to achieve a multiplexed, multi-staged plurality of Liquid Tissue preparations simultaneously from a single histopathologically processed biological sample, where the protocol for each Liquid Tissue preparation imparts a distinctive set of biochemical effects on biomolecules procured from histopathologically processed biological samples and which when each of the preparations is analyzed can render additive and complementary data about the same histopathologically processed biological sample.

23 Claims, 5 Drawing Sheets

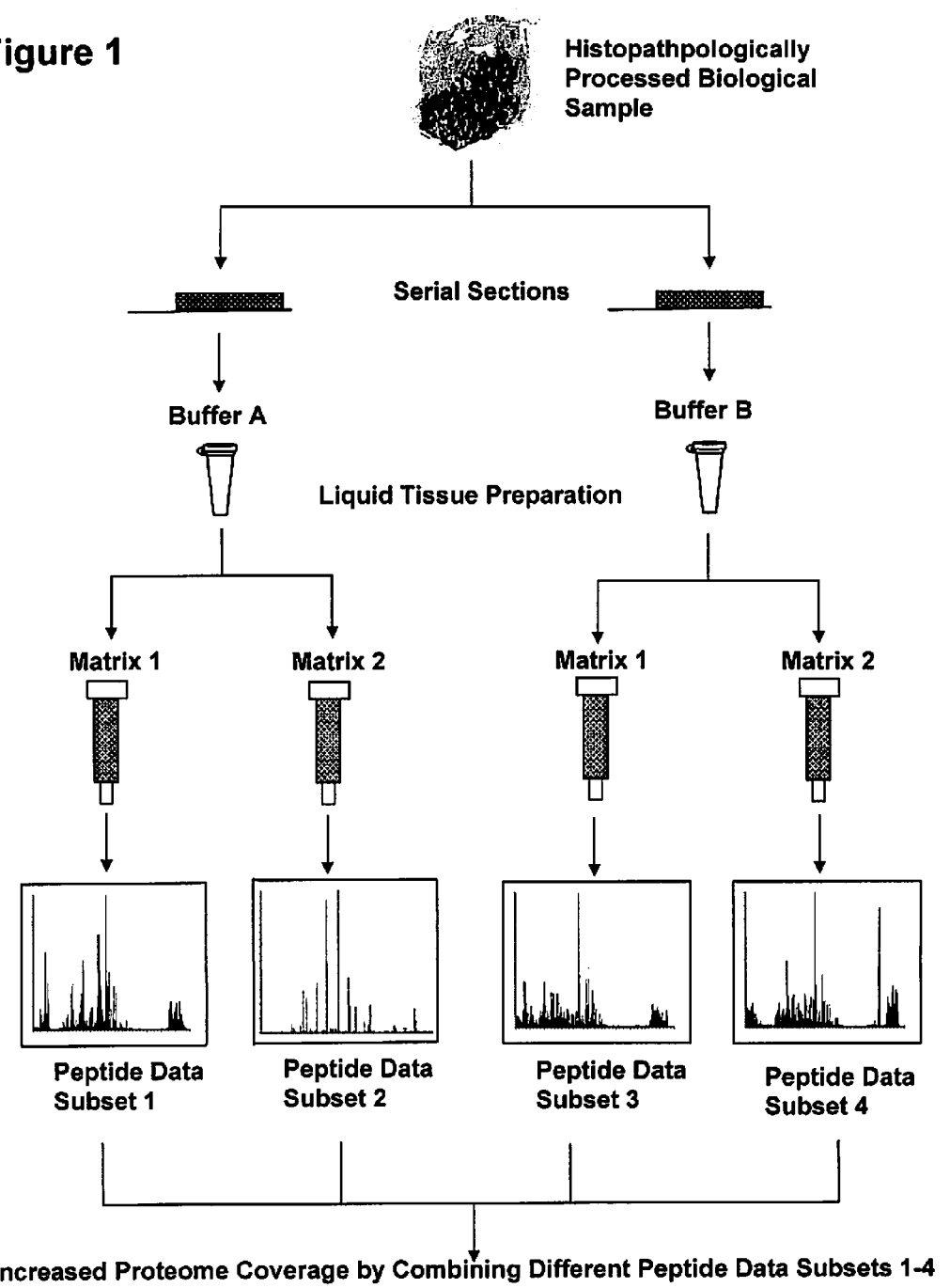

Figure 2

Step 1) Histopathologically Processed Tissue Sample

Step 2) Plurality of Liquid Tissue Preparations Under Different Buffer Conditions Ex. 1) Tris
2) Ammonium Bicarbonate
3) heat
4) methanol
5) glycerol

Step 3) Matrix-based separation

Ex. 1) reverse-phase
2) normal-phase
3) metal (Ca, Ga, Nl, Fe, Zr)
4) strong cationic
5) weak cationic

Step 4) Mass Spectrometry Analysis of Individual Liquid Tissue Preparations

Step 5) Protein Identification and Combining Data into Single DataSet

Liquid Tissue – Ammonium Bicarbonate preparation / TIC / Base peak chromatogram

Figure 5

| | |
|---|---|
| Ammonium Bicarbonate: | 332 fully tryptic peptides > 278 unique peptides = 220 unique proteins |
| Ammonium Bicarbonate: + 20%MeOH | 312 fully tryptic peptides > 272 unique peptides = 211 unique proteins |
| Results Summary: | 354 total unique proteins identified from this histopathologically processed tissue<br>- 77 unique proteins are similar between the two samples<br>- 143 unique to AMB preparation<br>- 134 unique to AMB/20% MeOH preparation |

MULTIPLEX LIQUID TISSUE™ METHOD FOR INCREASED PROTEOMIC COVERAGE FROM HISTOPATHOLOGICALLY PROCESSED BIOLOGICAL SAMPLES, TISSUES AND CELLS

RELATED APPLICATION

This application is a continuation of U.S. Ser. No. 11/915,582, filed Jul. 14, 2008 now U.S. Pat. No. 7,906,301; which is a national stage application of International Application No. PCT/US2006/020166, filed May 25, 2006; which claims the benefit of U. S. Provisional Application No. 60/684,167, filed May 25, 2005, the entire contents of the applications being incorporated herein by reference in their entirety.

FIELD OF THE INVENTION

The invention provides compositions and methods for the multiplex analysis of biological samples prepared from formalin-fixed tissue specimens.

BACKGROUND

For over a hundred years, public and academic medical universities and institutions, pathology clinics, private biomedical institutions, tissue archives, hospitals, and museums have been preserving biological specimens with formalin and other chemical fixatives such as formaldehyde and ethyl alcohol. The most common fixative is formalin. Formalin is used as a fixative because of it superior ability to preserve both tissue structure and cellular morphology. This has resulted in the wide use of formalin for the successful preservation of histologic sections for traditional microscopic analysis. Formalin fixation is so effective in preserving tissue structure and cellular morphology that the formalin archive is a veritable treasure trove containing millions of samples. Within this archive are biological samples of healthy tissue, tissue samples from virtually every known human disease, and a multitude of preserved life forms.

Formalin fixation occurs through the cross-linking of proteins within the biological specimen. These protein cross links, while providing excellent cellular morphology preservation, also renders the fixed sample relatively insoluble. Because of these protein cross-links, the types of assays that can be performed on a formalin-fixed sample are limited in number, unable to provide quantitative results and lack sensitivity. In fact, formalin fixed biological samples are virtually unusable in many modern assay techniques, which are both highly quantitative and sensitive.

Thus, there is an unmet need in the industry to use histologically processed samples to generate preparations from these samples that contain subsets of biomolecules contained in the samples, and to combine these subsets to generate a library containing the entirety of the biomolecular components of a given histopathologically processed biological sample.

SUMMARY OF THE INVENTION

In general, the present invention relates to detection of diseases such as cancer by analysis of proteins contained in Liquid Tissue preparations obtained from histologically processed samples, such as formalin-fixed tissue.

In one aspect, the invention provides a method of generating a multiplexed Liquid Tissue preparation by contacting a first biological sample with a first buffer solution and a second biological sample with a second buffer solution, heating the first and second contacted samples at a temperature and for a time sufficient to substantially reduce the protein cross-links present in the biological samples, and treating the heated first and second samples with an effective amount of a proteolytic enzyme for a time sufficient to substantially reduce the proteins to individual peptides, thereby generating a multiplexed Liquid Tissue preparation. Detection comprises mass spectrometry (e.g., matrix-assisted laser desorption/ionization-time of flight mass spectrometry (MALDI-TOF), liquid chromatography electrospray ionization tandem mass spectrometry (LC-ESI-MS/MS), or surface enhanced laser desorption ionization (SELDI) mass spectrometry), immunohistochemistry, ELISA, Western blotting, polyacrylamide gel electrophoresis, synthetic aptamer binding analysis, or isoelectric focusing analysis.

In embodiments of the invention, the method also includes the step of detecting the presence of least one protein analyte in the first sample and at least one protein analyte in the second sample. In other embodiments, the first buffer is chemically distinct from the second buffer. In other embodiments, the method also includes the step of comparing the analytes detected in the first and second samples with one or more reference analytes; the reference analyte may be obtained from a subject having a disease or condition. Further, the invention provides the additional step of separating the first sample using a first separation system and separating the second sample using a second separation system, thereby generating a separated multiplexed Liquid Tissue preparation. The first separation system and the second separation system separately comprise a chromatography matrix. The first separation system may be distinct from the second separation system.

Optionally, the first biological sample and the second biological sample comprise adjacent serial sections.

The invention also provides the multiplexed Liquid Tissue preparation generated by these methods.

In another aspect, the invention provides a method of analyzing a tissue proteome by contacting a first biological sample with a first buffer solution and a second biological sample with a second buffer solution, heating the first and second contacted samples at a temperature and for a time sufficient to substantially reduce the protein cross-links present in the biological samples, treating the heated first and second samples with an effective amount of a proteolytic enzyme for a time sufficient to substantially reduce the proteins to individual peptides, and detecting the presence of at least one protein analyte in each of the first and second treated samples, thereby analyzing a tissue proteome. Optionally, the first biological sample and the second biological sample comprise adjacent serial sections.

In certain embodiments, the invention provides the additional step of separating the treated first sample using a first separation system and separating the treated second sample using a second separation system.

In other embodiments, the method includes at least n biological samples and n buffer conditions, wherein n is a positive whole number between 3 and 100.

In another aspect, the invention provides a kit for preparing a multiplexed Liquid Tissue preparation that includes a histopathologically processed biological sample, a buffer or buffer reagents, a proteolytic enzyme and one or more chromatography matrices. In some embodiments the kit also includes an additive or additive reagents.

In some embodiments, the histopathologically processed biological sample comprises a substantially homogeneous population of tissues or cells. The histopathologically processed biological samples are formalin-fixed tissue/cells, formalin fixed paraffin embedded (FFPE) tissue/cells, FFPE tissue blocks and cells from those blocks, or tissue culture cells that have been formalin fixed and/or paraffin embedded.

The methods of the invention also include the step of removing any paraffin or embedding compound in the histopathologically processed biological sample, such as by adding an organic solvent; heating; heating and adding a buffer; or heating and adding an organic solvent.

In other embodiments, the methods of the invention also include the step of mechanically disrupting the biological sample by, for example, manual homogenization, vortexing, or and physical mixing. In some embodiments the heating and/or proteolytic enzyme treatments are carried out in the presence of a reaction buffer such as Tris and/or ammonium bicarbonate, and generally has a pH in the range of about 6.0 to about 9.0. The buffer in some cases contains an additive such as glycerol, methanol, glycogen, or polyethylene glycol (PEG).

In other embodiments, the methods of the invention include the step of using a plurality of chromatography matrices to fractionate a single individual Liquid Tissue preparation into many different fractions based on the biochemical retention properties of the chromatography matrices. Each fraction is suitable for use in biochemical assays.

Generally, the proteolytic enzyme is proteinase K, chymotrypsin, papain, pepsin, trypsin, pronase, or endoproteinase Lys-C.

Mass spectrometry is a preferred means for detecting analytes contained in the Liquid Tissue preparations. MALDI-TOF, SELDI-TOF, LC-MS/MS, LC-ESI-MS/MS, and LC-FTICR-MS/MS are used to detect the presence or absence of one or more analytes in the Liquid Tissue preparations. The analytes can be, e.g., proteins or peptides derived from a protein.

The invention further provides methods of analyzing a plurality of multiplexed Liquid Tissue preparations by immobilizing a plurality of Liquid Tissue preparations on a support surface, such that each preparation is immobilized at a discrete location of the surface; contacting the support surface with a reagent of known binding affinity, and detecting the presence or absence of binding of the reagent of known binding affinity to the support surface. The plurality of Liquid Tissue preparations can be spotted into the support surface by manual spotting, ink-jetting, robotic contact printing, robotic non-contact printing, or piezoelectric spotting. The reagents of known binding affinity may be, for example, antibodies and antibody fragments, single domain antibodies, engineered scaffolds, peptides, nucleic acid aptamers, a receptor moiety, affinity reagents, small molecules, protein ligands, and the like. The support surface contains a material such as glass, derivatized glass, silicon, derivatized silicon, porous silicon, plastic, nitrocellulose membranes, nylon membranes, or PVDF membranes.

All the methods of the present invention provide for the fractionation or separation of the Liquid Tissue preparations prior to mass spectrometry or other detection means. Such a separation can include a matrix-based separation step. However, Liquid Tissue preparations can be prepared and analyzed without further separation prior to analyte detection or analysis.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

These and other objects of the present invention will be apparent from the detailed description of the invention provided below.

BRIEF DESCRIPTION OF THE DRAWINGS

The foregoing and other features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 is a flow chart illustrating the method to achieve a multiplexed plurality of unique Liquid Tissue biomolecule preparations simultaneously from a single biological sample of the present invention.

FIG. 2 describes the steps involved in FIG. 1.

FIG. 5 shows the data analysis from these mass spectrometry chromatograms indicating that a total of 77 proteins were commonly identified from these two separate preparations. In contrast, a total of 143 proteins were identified in the ammonium bicarbonate-only preparation that were not identified in the preparation with ammonium bicarbonate buffer in which 20% methanol was added to the buffer prior to tryptic digestion. In addition, a total of 134 unique proteins were identified in the 20% methanol/ammonium bicarbonate buffer that were not identified from the ammonium bicarbonate buffer alone preparation.

DETAILED DESCRIPTION

Figure 3:
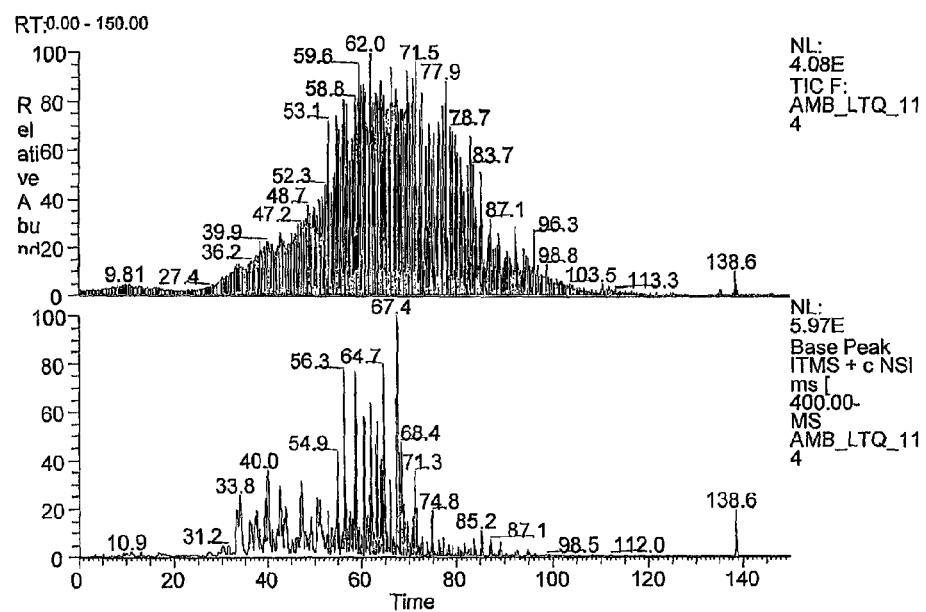
FIG. 3 shows a base chromatogram analysis by mass spectrometry of one of two separate and distinct Liquid Tissue preparations from the same histopathologically processed biological sample for identification of similar and different proteins. This particular preparation was made by incubation and tryptic digestion in 100 mM ammonium bicarbonate buffer.
Figure 4:
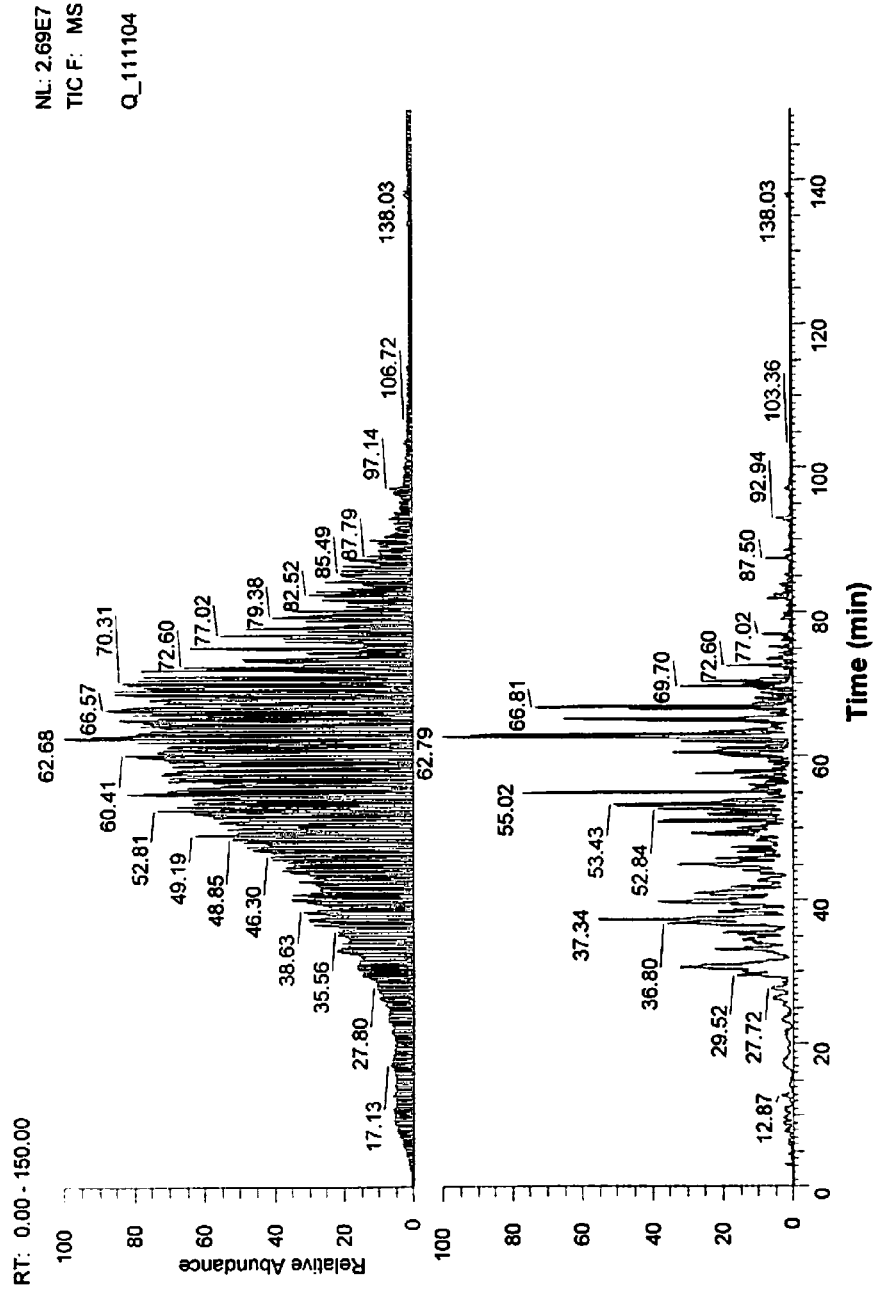
FIG. 4 shows a base chromatogram analysis by mass spectrometry of a second and distinctly different Liquid Tissue preparations from the same histopathologically processed biological sample as in FIG. 3 for identification of similar and different proteins. This sample was prepared using the same buffer as the sample in FIG. 3, with the addition of 20% methanol prior to heating and tryptic digestion.

The present invention provides methods for multiplexing Liquid Tissue preparations derived from histopathologically processed tissue sections.

Previously, the present inventors have found that histopathologically processed biological samples can be heated in a reaction buffer, followed by protease treatment, to provide materials, herein termed Liquid Tissue preparations, that are rich in molecular information regarding the original biological sample. See U.S. Ser. No. 10/796,288, filed Mar. 10, 2004, the contents of which are incorporated by reference in their entirety.

As used herein and in the appended claims, the singular forms "a," "and," and "the" include plural reference unless the context clearly dictates otherwise. Thus, for example, reference to "a protein" is a reference to one or more proteins and includes equivalents thereof known to those skilled in the art, and so forth.

Biological Samples

Histopathologically processed biological samples can include whole organisms, samples obtained from biopsy, diagnostic surgical pathology, tissue samples, body fluids (e.g., blood, plasma, serum, saliva, semen, cervical secretions, saliva, urine, tears, sweat, breast milk, and amniotic fluids), cellular or viral material, or any other biological sample that has been histopathologically processed.

Examples of histopathological processing of biological samples include, but are not limited to: formalin fixation of whole organisms; formalin fixation of tissues or cells; formalin fixation/paraffin embedding of tissues or cells; and formalin fixation and/or paraffin embedding of tissue culture cells.

Histopathological processing typically occurs through the use of a formalin fixative. Formalin is used widely because it is relatively inexpensive, easy to handle, and once the formalin-fixed sample is embedded in paraffin the sample is stored easily. Additionally, formalin is often the fixative of choice because it preserves both tissue structure and cellular morphology. Although the exact mechanism may not be understood fully, fixation occurs by formalin-induced cross-linking of the proteins within the biological specimen. Due to these protein cross-links, formalin fixation has found wide success in the traditional microscopic analysis of histologic sections.

The sheer volume of formalin-fixed specimens cannot be overstated. For nearly the last one hundred years, biological specimens have been commonly fixed in formalin or formalin fixed/paraffin wax-embedded (FFPE) blocks. Universities and museums have vast archives of plants and animals that are formalin-fixed. Hospitals, in the course of diagnostic surgical pathology, have established large formalin-fixed collections that contain tissues from nearly every known disease in addition to normal, healthy tissue. Due to the need to retain these clinical tissue samples in case further testing is required, these archives around the world now contain millions of FFPE samples.

Liquid Tissue Preparations

The invention described herein provides for the use of Liquid Tissue preparations obtained from histopathologically processed biological samples. Generally, the Liquid Tissue preparations contain substantially all of the biomolecules contained within the sample, including but not limited to proteins, glycoproteins, nucleic acids (e.g., DNA, RNA), lipids, glycolipids, and cell organelle-derived molecules. As used herein, the term "protein" encompasses all proteins, including polypeptides, protein fragments, oligopeptides, and peptides containing two or more amino acids connected by peptide bonds.

The biomolecules contained within the Liquid Tissue preparation are useful as "analytes", either in a whole and intact form or and component thereof, if the biomolecule is detectable, such as by mass spectroscopy or by binding to a reagent of specific binding affinity. By way of non-limiting example, analytes useful herein include peptides generated by proteolytic digestion of proteins contained in the Liquid Tissue preparation.

In addition, the Liquid Tissue preparations described and used herein can be subjected to additional manipulations, such as fractionation by chromatography or other means, dilution, treatment with enzymes or other modifying agents.

Methods of Preparing Liquid Tissue Preparations

In general, Liquid Tissue preparations are generated by contacting all or a portion of a biological sample (e.g., a formalin-fixed tissue section) with a buffer solution. The sample in solution is heated for a time and at a temperature sufficient to negatively affect (e.g., reverse) the formalin-induced protein cross-links. For example, the heating is performed at a temperature of about 60° C. to about 100° C. (e.g., at about 65° C., 75° C., 80° C., 85° C., 90° C., 95° C., 98° C., 100° C., 102° C., or 105° C.) from about 30 seconds to about 24 hours or more (e.g., for 5, 10, 15, 30, 45 seconds, or 1, 2, 3, 4, 5, 10, 15, 30 or 45 minutes or 1, 2, 3, 4, 5, 7, 10, 14, 18, or 24 hours). Without being bound by any theory, the present inventors believe that the negative affect of temperature on the protein cross-links appears to involve some form of releasing, reversing, or partial modification of the cross-links. Generally, as used herein, the term "buffer" refers to a buffer which has a specific pH in the range of 1.0 to 9.0. Both specific pH and buffer types are selected based upon the required conditions, such as the proteolytic enzyme used. Both buffer type and specific pH requirements are known to those well versed in the arts. For additional details, see patent application U.S. Ser. No. 10/796,288.

The heated solution is then modified by adding at least one enzyme to the histopathologically processed biological sample. Enzymes include proteases, nucleases, glycosidases, lipases, phospholipases, phosphatases, and sulfatases. In a preferred embodiment, the enzyme is a proteolytic enzyme. Proteolytic enzymes are believed to augment the negative effect of heating on formalin-induced protein cross-links. One of skill in the art would recognize the time, temperature, and quantity of the enzyme sufficient to negatively affect the formalin-induced protein cross-links. Examples of proteolytic enzymes that are suitable for use in the present invention include but are not limited to trypsin, proteinase K, chymotrypsin, papain, pepsin, pronase, and endoproteinase Lys-C. Advantageously, the protease treatment is carried out following the heating step described above. The protease treatment is advantageously carried out at a temperature that is optimal for maximum activity of the protease, such as about 30° C. to about 60° C. Proteolytic enzyme treatment generally lasts for a period of about 1 minute to about 24 hours, such as 1, 2, 3, 5, 10, 15, 40 or 45 minutes, or 1, 2, 3, 4, 5, 10 18 or 24 hours.

If the sample is embedded in paraffin or some similar material, the paraffin may be removed by, for example, adding an organic solvent, heating, heating and adding a buffer comprising ammonium bicarbonate or Tris, and/or heating and adding an organic solvent. Advantageously, this step is carried out prior to the main heating step. If the sample is heated as part of the process to remove paraffin, the heating need only be brief, for example a few minutes. This brief heating advantageously may be repeated two or more times to ensure maximum removal of paraffin.

At any stage the sample may be mechanically disrupted by, for example, manual homogenization, vortexing, and/or physical mixing. The simultaneous multiple Liquid Tissue preparations produced by these methods are subjected to a wide variety of biochemical assays including arrays, protein arrays, and mass spectrometry.

In one embodiment of the current invention, the Liquid Tissue preparation is fractionated into distinct and separate biomolecules that may be collected separately. Examples of biomolecule fractions that can be collected include but are not limited to protein, glycoproteins, nucleic acids (e.g., DNA, RNA), glycolipids, and lipids. Fractionation techniques are well known in the arts and include but are not limited to, spin column fractionation, immunoprecipitation, gradient centrifugation, HPLC and drip column fractionation. Other fractionation methods are well known in the art.

In another embodiment of the current invention, the Liquid Tissue preparation is modified by the addition of one or more detergents, including for example Nonidet-P-40, SDS, Tween-20, Triton-X, and sodium deoxycholate. The detergent is added prior to the protease treatment step (before or after heating), in which case the nature of the detergent and its concentration is selected so as to not substantially inhibit the activity of the protease. Alternatively, the detergent is added after addition of the protease.

Multiplexing of Liquid Tissue Preparations

One embodiment of the invention provides for the generation of a plurality of multiplexed Liquid Tissue preparations from a single histopathologically processed biological sample where each of the individual multiplexed preparations consists of distinctly different biochemical properties such that subsequent analysis of all Liquid Tissue preparations from a single histopathologically processed sample render more experimental data about the biomolecules in the histopathologically processed biological sample than a single Liquid Tissue preparation can render by itself. The combination of a plurality of multiplexed Liquid Tissue preparations can be used to generate a tissue proteome, which is the complete collection of proteins found in a particular tissue under a particular set of conditions, such as the presence of a disease. Each individual Liquid Tissue preparation forms a representative subset library of the total library of biomolecules (the tissue proteome) that exist in that histopathologically processed biological sample.

Use of the Lysates

The method described herein is particularly useful because it can be used to obtain a plurality of multiplexed multi-use biomolecule lysates from a single histopathologically processed biological sample where each lysate is capable of being used with numerous experimental and diagnostic techniques to generate complementary information about the histopathologically processed biological sample, thereby providing new uses for the histopathologically processed archive. Examples of techniques that the plurality of preparations can be used with include but are not limited to are chromatography, protein arrays, Western blotting, immunoprecipitation, affinity columns, alternative splicing assays, and high throughput assays such as but not limited to one- and two-dimensional polyacrylamide gel electrophoresis (2D-PAGE), serial analysis of gene expression (SAGE), high performance liquid chromatography (HPLC), fast protein liquid chromatography (FPLC), matrix-assisted laser desorption/ionisation-time of flight mass spectrometry (MALDI-TOF), SELDI mass spectrometry, liquid chromatography, mass spectrometry, and ELISA assays. The skilled artisan will recognize that the lysates produced by the methods of the invention also may be used in a wide variety of additional assays.

The recent completion of the Human Genome Project, in addition to spurring dramatic advances in the field of genomics and proteomics, has demonstrated the vast potential of high throughput assays. Proteomics attempts to identify and quantify proteins in biological samples and is now attempting to determine the functions of all proteins in an organism, organ, or organelle, and how these proteins vary with time and physiological state.

Analyte Detection and Quantitation

Detection of one or more analytes is accomplished by any means known to those skilled in the art. A preferred detection means is mass spectroscopy, such as matrix-assisted laser desorption/ionization-time of flight mass spectrometry (MALDI-TOF), liquid chromatography electrospray ionization tandem mass spectrometry (LC-ESI-MS/MS), or surface enhanced laser desorption ionization (SELDI) mass spectrometry. Mass spectroscopic analyses are described in greater detail below.

Exemplary analytes are provided in Table 1.

Other detection means include but are not limited to are column chromatography, protein arrays, Western blotting, immunoprecipitation, affinity columns, alternative splicing assays, mutation analysis, nucleic acid amplification (for example PCR, LCR, and T7-based RNA amplification), labeled probes for microarray analysis, RFLP analysis, Southern blotting, and high-through put assays such as but not limited to one- and two-dimensional polyacrylamide gel electrophoresis (2D-PAGE), serial analysis of gene expression (SAGE), HPLC, FPLC, liquid chromatography, ELISA assays, Quantitative RT-PCR, Single Nucleotide Polymorphism detection, genotyping and protein and nucleic acid sequencing. See, Shi et al., Antigen retrieval techniques: current perspectives. J Histochem Cytochem. 2001 49(8): 931-73; Espina et al., Protein microarrays: molecular profiling technologies for clinical specimens. Proteomics. 2003 3(11): 2091-100; Bons et al., Protein profiling as a diagnostic tool in clinical chemistry: a review. Clin Chem Lab Med. 2005 43(12):1281-90; Loor et al., Evaluation of a human pancreas-specific antigen by enzyme-linked immunosorbent assay. Clin Chim Acta. 1981 117(3):251-8; and Ikeda et al., Extraction and analysis of diagnostically useful proteins from formalin-fixed, paraffin-embedded tissue sections. J Histochem Cytochem. 1998 46(3): 397-403.

When the analyte of interest is a protein or peptide, the Liquid Tissue preparation is generally in a soluble liquid form and is representative of the total protein content of the cells procured from the starting histopathologically processed biological sample. The preparation is used in any number of protein identification, analysis and expression assays described herein or known to the skilled practitioner.

When the analyte of interest is DNA, the Liquid Tissue preparation is in a soluble liquid form and is representative of the total DNA content of the cells procured from the starting histopathologically processed biological sample. The DNA extract can be placed in any number of DNA and/or RNA gene identification analyses and monitoring assays designed to determine variations in DNA including but not limited to the analysis of gene structure, genetic variability, single nucleotide polymorphisms and mutation analyses.

When the analyte of interest is RNA, the Liquid Tissue preparation is in a soluble liquid form and is representative of the total RNA content of the cells procured from the starting histopathologically processed biological sample. The RNA extract can be placed in any number of RNA and/or gene identification analysis and gene expression analysis and quantitative RT-PCR analysis In certain embodiments it is useful to quantitate the detected analytes. This quantitation is performed by, e.g., isotopic labeling of the proteins; methods for isotope labelling include SILAC (stable isotope labelling with amino acids in cell culture), ICAT (isotope coded affinity tagging), and ITRAQ (isotope tags for relative and absolute quantitation). Alternatively, quantitation is performed by the use of AQUA peptides (See, Stemmann et al., Dual inhibition of sister chromatid separation at metaphase, Cell 107: 715-726 (2001)).

In certain embodiments the analyte detected in the Liquid Tissue preparation is compared with a reference analyte. A reference analyte is any analyte obtained from a subject known to have or not have the disease, condition, or syndrome. In certain embodiments, a reference analyte comprises a database.

Mass Spectrometry Assays

A specific example of a proteomic assay capable of generating information about protein expression patterns is mass spectrometry. Mass spectrometry can be conducted in a highly parallel manner, is highly sensitive, and is capable of generating an enormous amount of data in a single experiment. The data generated by a single mass spectrometry analysis of a single Liquid Tissue protein preparation is so voluminous that specialized computer software is required to read and analyze the data that is generated.

In order to significantly link a single candidate marker to any disease, a large number of cases must be screened to generate definitive correlations. However, obtaining enough biological samples with known disease outcomes in a frozen or stable and storable state that is not chemically fixed is a limiting factor. A possible solution to this limitation would be the use of the worldwide archive of diseased tissue and cells. The methods of the current invention are particularly useful because a plurality of multi-use Liquid Tissue preparations from a single histopathologically processed biological sample allows collection of large amounts of experimental data from a single sample in a high throughput fashion by mass spectrometry.

In one type of mass spectrometry analysis, a single Liquid Tissue preparation is subjected to one of many forms of chromatography where each form is directly attached to a high-resolution mass spectrometer. As fractions come off the chromatography column they are instantly analyzed by the mass spectrometer by nanospray technology. Sophisticated computer programs translate all the ion information obtained by nanospray analysis of every chromatography fraction into data containing identification of as many peptides as the instrument is able to resolve. Collecting peptide identification about each and every chromatography fraction, and pooling these data can positively identify hundreds to thousands of individual peptides from the starting Liquid Tissue preparation, which translates to the ability to positively identify expression of hundreds of suspected biomarkers directly from a single Liquid Tissue preparation from a single formalin fixed archival tissue. The method of this invention is to prepare a plurality of Liquid Tissue preparations from a single cellular region of sufficient cellular homogeneity from a single formalin fixed archival tissue sample and perform the type of mass spectrometry described herein, where each of the Liquid Tissue preparations is composed of different and unique biochemical properties so that when analyzed by mass spectrometry a different and unique subset of peptides are positively identified from each and every individual Liquid Tissue preparations.

Thus, the present invention provides the ability will result in the ability to combine data from many different multiplexed Liquid Tissue preparations from the same cellular region of a single formalin fixed tissue sample rendering the combined identification on many more proteins than if a single Liquid Tissue preparation were analyzed only once. In this way, thousands (and possibly tens of thousands) of suspected biomarkers can be identified, discovered, and analyzed in a single experiment directly from a single cellular region obtained from a single formalin fixed archival tissue. By performing this multiplex strategy for a single formalin fixed tissue sample across many formalin fixed tissue samples of the same disease and pathology, it becomes possible to link thousands to tens of thousands of potential biomarkers to a specific histologically identified disease process. This translates to providing statistical significance in the quest to link specific proteins to the pathological manifestation of the progression of diseases such as cancer and neurological disorders.

Specific mass spectrometry instruments and data analysis computer programs to perform these experiments are commercially provided by a number of vendors and instruments manufacturers. These companies include ThermoElectron (San Jose, Calif.), Bruker Daltonics (Billerica, Mass.), and Applied Biosystems (Foster City, Calif.).

As used herein, the term "nanospray" also refers to the terms "ionspray" and "electrospray". All of these terms can be used interchangeably. As used herein, the term "sufficient homogeneity" refers to a population of tissues or cells that possess similar pathological characteristics or traits based on selection criteria. An example of selection criteria includes but is not limited to histopathological selection criteria that are well known in the relevant arts. Examples of methods of "obtaining" a biological sample include, but are not limited to, using a manual core punch, tissue punch, tissue scrape, laser-based microdissection, and other techniques known to one of skill in the art The amount of biological sample required to carry out the invention will vary depending on the specific type of assay being conducted on the sample.

Liquid Tissue Arrays

In the present invention of procuring a plurality of different biomolecular preparations from a single histopathologically processed sample to achieve complementary and additive data about the histopathologically processed sample, each lysate of biomolecules forms a representative library of specific biomolecules that directly reflects the status of a subset of biomolecules as they previously resided in the pathologically processed biological sample.

The resulting procured biomolecules can be placed in an arrayed format for the simultaneous biochemical analysis of multiple Liquid Tissue preparations obtained from a single histopathologically processed sample or multiple and different histopathologically processed biological samples to achieve a high throughput biochemical assay format for the molecular analysis and profiling of pathologically processed biological samples. One example of such a high throughput array assay format would be the development of a Liquid Tissue protein array such that tissue protein lysates derived from the processed histopathological tissue and procured as stated above are arrayed in an ordered and defined pattern as small spots of protein on a solid support substrate, where each spot is a representative library of the expressed proteins, and characteristics of those expressed proteins, that resided in the pathologically processed biological sample, and that when assayed by a number of various biochemical protein analysis formats, such as immuno-based protein identification binding assays, do directly reflect the expression pattern and characteristic of the proteins as they relate to the pathology and histology of the pathologically processed biological sample from which the proteins were procured.

When the biomolecule is a protein or peptide, the plurality of protein or peptide extracts is in a soluble liquid form where each preparation contains and is representative of a subset of the total protein content of the cells procured from the starting histopathologically processed biological sample. The multitude of Liquid Tissue protein extracts can be placed in any number of protein identification, analysis, and expression monitoring assays including, but not limited to, mass spectrometry and protein microarrays that contain representative libraries of proteins from pathologically and histologically defined populations of histopathologically processed biological sample and as these analyses relate to the histology, disease state, and pathology of the histopathologically processed biological sample.

Multiple Liquid Tissue preparations obtained from multiple different histopathologically processed biological samples can be placed in an array format. A specific example of a high-throughput assay is the protein array. Protein arrays are highly parallel (multiplexed) and can be conducted in miniature (microarray). Protein arrays are quick, usually automated, highly sensitive, and capable of generating an enormous amount of data in a single experiment. The protein array is essentially a miniaturized version of the familiar ELISA or dot blotting immunoassay. Similar to ELISA and dot blots, protein array results are usually obtained using optical detection methods, for example fluorescent detection. The data generated by a single protein array experiment often is so voluminous that specialized computer software is useful to read and analyze the data that is generated.

In one type of protein array analysis, specific capture reagents of known binding affinity, such as antibodies, are immobilized or spotted onto a support surface in a known positional manner, thus forming the protein array. The Liquid Tissue preparation is then contacted with the protein array. Because the immobilized binding proteins on the support surface have a specific affinity for an individual protein or marker, protein arrays are able to detect target molecules or marker proteins in the Liquid Tissue preparation. By immobilizing the specific capture reagents in known locations on the support surface, protein identification and the presence of marker proteins can be determined by x, y positional information. In addition, since differences in protein levels within complex samples can be easily measured, accurate quantitative differential analysis can also be performed. Detection is achieved through a number of methods known to those well versed in the art. Examples include but are not limited to: secondary antibodies in sandwich assays, direct labeling of analytes, dual color labeling, mass spectrometry, surface plasmon resonance, and atomic force microscopy.

An alternative type of protein array analysis places tissue/cell lysates in an arrayed format, for example on a solid support. Multiple lysates from different samples may be arrayed on a single surface in a positionally identifiable manner. Reagents of known binding specificity, such as antibodies, that bind to target biomolecules or markers are then added. The main difference between the two major types of array analyses described herein is that in the first type of protein array, the expression of many different proteins across a single source of protein (a single cancer tissue for example) can be determined. In contrast, by the other type of protein array analysis, one can assay for the expression of one protein at a time across many different sources of protein (many different cases of cancer tissues for example). The lysate may be fractionated prior to immobilization on the array, and protein containing fractions of the lysates may be used to prepare the array. The skilled artisan will recognize also that other fractions of the lysates can be used to prepare arrays. For example, DNA and/or RNA containing fractions can be immobilized on suitable surfaces to prepare nucleic acid arrays.

Specific reagents of known binding affinity in protein arrays advantageously are antibodies or antibody fragments, but may also be single domain antibodies, engineered scaffolds, peptides, nucleic acid aptamers, small molecules such as drugs, for example, protein ligands, or other specific binding proteins known in the relevant art. Antibodies may be either polyclonal or monoclonal, or a portion or fragment of an antibody capable of binding antigenic sites, and are available from the usual commercial sources such as Sigma-Aldrich Co. (St. Louis, Mo.).

Protein array support surfaces include but are not limited to glass (such as slides), silicon, porous silicon, nylon, PVDF or nitrocellulose membranes and the like, or beads and are available from a variety of commercial sources. Alternatively, specialized chips have been developed for protein assays and are commercially available from, for example, Biotrove (Woburn, Mass.), Zyomyx (Hayward, Calif.) and Pontilliste (Mountain View, Calif.).

Specific capture reagents or Liquid Tissue preparations are spotted or immobilized onto the support surface by a number of techniques familiar to those knowledgeable in the arts. Examples include, but are not limited to, robotic contact printing, robotic non-contact printing, ink jetting, and piezo-electric spotting. If the capture reagent is a polymer that may be synthesized on a solid support, such as a nucleic acid, the capture reagent may be prepared directly on the support by, for example, photolithography. A number of automated commercial spotters are available from, for example, Packard Bioscience (Meriden, Conn.) and manual spotting equipment also is commercially available from, e.g. V & P Scientific (San Diego, Calif.).

The present invention includes articles of manufacture, such as "kits". Such kits will typically be specially adapted to contain in close compartmentalization each container holding a component useful in carrying out the preparation of the multitude of Liquid Tissue preparations according to the methods and compositions taught herein. In a particular embodiment, the present invention provides compositions that contain a histopathologically processed biological sample, a plurality (more than one) of reaction buffers, a plurality than one) of additives to the buffer, and an agent of chromatography (column or tip) with different and varied chromatography matrices.

EXAMPLES

The following examples are provided to further illustrate and to facilitate the understanding of the invention. These specific examples are intended to be illustrative of the invention and are not intended to be limiting.

Example 1

Generation of a Plurality of Liquid Tissue Preparations

FIG. 1 is a flow chart illustrating the embodiment of the present invention, comprising a method of preparing a plurality (in buffer A and buffer B) of Liquid Tissue preparations of peptides and subsequently passing said preparations through different chromatography methods (Matrix 1 and Matrix 2) to obtain a total of four different peptide preparations from the same starting sample and where complementary datasets can be developed by mass spectrometry so that upon combining the data from assaying all of the various preparations by mass spectrometry more information about the proteome is obtained than if analysis of a single preparation were performed.

Example 2

Use of Multiple Buffers in the Generation of a Plurality of Liquid Tissue Preparations FIG. 2 is a flow chart describing each of the steps involved in the present invention. These steps need not be performed in any particular order, and serve as a non-limited description as follows:

a. imparting specific selection criteria, based on histology, to a biological sample to achieve an enrichment of specific homogeneous biological tissue/cell populations, such as that which is achieved by tissue microdissection methods, before imparting biomolecule procurement in the form of Liquid Tissue preparation;
b. collecting a plurality (more than one) of serial regions of tissue/cells from this histopathologically processed biological sample to achieve a plurality of preparations from the same sample;
c. adding a specific pH-adjusted (ranging from pH=6.0 to pH=9.0) buffer to each of the plurality (more than one) of said procured biological sample for stabilization of peptides, peptide fragments, proteins, and enzymes;
d. utilizing a different and unique buffer for each of the additional plurality (more than one) of preparations where each buffer can consist of either a starting buffer compound of different makeup or result from addition of different additives such methanol, glycerol, polyethylene glycol, or any other organic or inorganic reagents, or both;
e. imparting physical disruption to said plurality of preparations (more than one) from procured biological sample by manual homogenization, vortexing, and/or physical mixing;
f. heating each of the resulting physically disrupted plurality of preparations of the biological sample at an elevated temperature in the range of from about 37° C. to about 100° C. for a period of time from about 5 minutes to about 5 hours;
g. adding one or more proteolytic enzyme(s), for example, proteinase K, collagenases, chymotrypsin, papain, pepsin, elastase, hyaluronidase, trypsin, pronase, neuraminidase, to said each of the plurality of physically disrupted biological sample preparations for a period of time from about 10 minutes to about 24 hours at an elevated temperature from about 37° C. to about 65° C.;
h. molecularly fractionating each of the plurality of resulting biological sample preparations by spin column fractionation, immunoprecipitation, gradient centrifugation, HPLC, drip column fractionation, matrix-based separation, or tip column chromatography in order to separate and retain specific molecular fractions, resulting in the procurement of different biomolecules in different and collectable fractions; procuring and purifying from each of the resulting distinctly different Liquid Tissue preparations specific subcellular and molecular fractions for the analysis of different biomolecules for subsequent biochemical assays.

Example 3

Preparation of a Plurality of Liquid Tissue Preparations from a Single Formalin Fixed Tissue Sample 1. Cut two 7 um thick serial tissue sections from the same formalin fixed paraffin embedded tissue block onto standard glass slides.
2. Heat both tissue section slides at 60° C. for 1 hour.
3. Remove paraffin from the tissue by standard methods with xylene.
4. Rehydrate the tissue on both slides in decreasing ethanol washes with the final wash being in water.
5. Remove residual water from tissue by tipping slides on their sides and wiping edge of slides with an absorbent wipe.
6. Perform a needle scrape of a 5 mm×5 mm region from the tissue section (slide 1) and place into a single silanized or low protein binding 1.5 ml microcentrifuge tube (tube A).
7. Perform a needle scrape of the same exact region and area from the next serial section (slide 2) into a second silanized or low protein binding 1.5 ml microcentrifuge tube (tube B).
8. Add 20 ul of 100 mM ammonium bicarbonate buffer to tube A.
9. Add 16 ul of 100 mM ammonium bicarbonate buffer and 4 ul 100% methanol to tube B.
10. Heat both tubes at 95° C. for 90 minutes. Every 20 minutes check both tubes and shake the buffer that has formed a condensation in the cap of both tubes down to the bottom of the tubes so that the buffer volume covers the tissue.
11. Microcentrifuge both tubes at 10,000 rpm for 1 minute
12. Place tubes on ice to cool.
13. Add 1.0 ul of trypsin to each tube and gently mix.
14. Incubate both tubes for at least one hour at 37° C. This step can proceed overnight to a maximum of 24 hours incubation time.
15. Microcentrifuge each tube at 10,000 rpm for 1 minute.
16. Heat both tubes at 95° C. for 5 minutes.
17. Microcentrifuge each tube at 10,000 rpm for 1 minute and place on ice.
18. The resulting plurality of multi-use Liquid Tissue preparations may be either used in subsequent assays or stored at −20° C. until ready for use.
19. One example of assaying these distinct preparations is as follows:
    a. Divide each tube into two separate and equal aliquots to render tubes A.1, A.2, B.1, and B.2.
    b. Add TFA to each tube to a final concentration of 0.1% TFA.
    c. Pass the volume from tube A.1 through a pipette chromatography tip containing C18 chromatography matrix 25 times to retain digested peptides on the chromatography matrix.
    d. Wash the tip five times with 20 ul of $H_2O$ each wash.
    e. Elute the bound peptides from the tip with 20 ul of 85% acetonitrile (ACN).
    f. Perform the same chromatography process on the buffer volume in tube B.1 in the exact same fashion as described in steps 21-23.
    g. Pass the volume from tube A.2 through a pipette chromatography tip containing IMAC chromatography matrix 25 times to retain digested peptides on the chromatography matrix.
    h. Wash the tip five times with 20 ul of $H_2O$ each wash.
    i. Elute the bound peptides from the tip with 20 ul of 85% acetonitrile (ACN).
    j. Perform the same chromatography process on the buffer volume in tube B.2 in the exact same fashion as described in steps 25-27.
    k. Analyze the subset of peptides each tube by mass spectrometry utilizing one or more methodologies for LC-ESI-MS/MS.
    l. Collect protein and peptide identification data for each of the mass spectrometry analyses for each of the distinct and unique Liquid Tissue preparations as described.
    m. Pool the data from each of the four distinct Liquid Tissue preparations to generate the total number of proteins identified as expressed from the one histopathologically processed biological sample.

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

TABLE 1

| GenBank Accession | Number of Peptide analytes | Protein |
|---|---|---|
| P12111 | 42 | Collagen alpha 3(VI) chain precursor |
| P21333 | 30 | Filamin A (Alpha-filamin) (Filamin 1) (Endothelial actin-binding protein) (ABP-280) (Nonmuscle filamin) |
| P35749 | 25 | Myosin heavy chain, smooth muscle isoform (SMMHC) |
| P13533 | 22 | Myosin heavy chain, cardiac muscle alpha isoform (MyHC-alpha) |
| Q8WZ42 | 20 | Titin |
| P12882 | 19 | Myosin heavy chain, skeletal muscle, adult 1 (Myosin heavy chain IIx/d) (MyHC-IIx/d) |
| P17661 | 19 | Desmin |
| P12883 | 16 | Myosin heavy chain, cardiac muscle beta isoform (MyHC-beta) |
| P62736 | 14 | Actin, aortic smooth muscle (Alpha-actin 2) |
| P02768 | 13 | Serum albumin precursor |
| P08670 | 12 | Vimentin |
| P35609 | 12 | Alpha-actinin 2 (Alpha actinin skeletal muscle isoform 2) (F-actin cross linking protein) |
| Q14315 | 12 | Filamin C (Gamma-filamin) (Filamin 2) (Protein FLNc) (Actin-binding like protein) (ABP-L) (ABP-280-like protein) |
| P12109 | 11 | Collagen alpha 1(VI) chain precursor |
| P12814 | 11 | Alpha-actinin 1 (Alpha-actinin cytoskeletal isoform) (Non-muscle alpha-actinin 1) (F-actin cross linking protein) |
| P18206 | 10 | Vinculin (Metavinculin) |
| P09493 | 9 | Tropomyosin 1 alpha chain (Alpha-tropomyosin) |
| P68871 | 9 | Hemoglobin beta chain |
| Q05707 | 9 | Undulin 1 (Fragment) |
| P02545 | 8 | Lamin A/C (70 kDa lamin) |
| P07437 | 8 | Tubulin beta-1 chain (OK/SW-cl.56) |
| P12110 | 8 | Collagen alpha 2(VI) chain precursor |
| O15061 | 7 | Desmuslin |
| P06576 | 7 | ATP synthase beta chain, mitochondrial precursor (EC 3.6.3.14) |
| P55268 | 7 | Laminin beta-2 chain precursor (S-laminin) (Laminin B1s chain) |
| Q9UKX2 | 7 | Myosin heavy chain, skeletal muscle, adult 2 (Myosin heavy chain IIa) (MyHC-IIa) |
| P06732 | 6 | Creatine kinase, M chain (EC 2.7.3.2) (M-CK) |
| P98160 | 6 | Basement membrane-specific heparan sulfate proteoglycan core protein precursor (HSPG) (Perlecan) (PLC) |
| Q01995 | 6 | Transgelin (Smooth muscle protein 22-alpha) (SM22-alpha) (WS3-10) (22 kDa actin-binding protein) |
| P02647 | 5 | Apolipoprotein A-I precursor (Apo-AI) (ApoA-I) |
| P04792 | 5 | Heat-shock protein beta-1 (HspB1) (Heat shock 27 kDa protein) (HSP 27) (Stress-responsive protein 27) (SRP27) (Estrogen-regulated 24 kDa protein) (28 kDa heat shock protein) |
| P05976 | 5 | Myosin light chain 1, skeletal muscle isoform (MLC1F) (A1 catalytic) (Alkali myosin light chain 1) |
| P07355 | 5 | Annexin A2 (Annexin II) (Lipocortin II) (Calpactin I heavy chain) (Chromobindin 8) (p36) (Protein I) (Placental anticoagulant protein IV) (PAP-IV) |
| P15502 | 5 | Elastin precursor (Tropoelastin) |
| P22105 | 5 | Tenascin X precursor (TN-X) (Hexabrachion-like) |
| P35579 | 5 | Myosin heavy chain, nonmuscle type A (Cellular myosin heavy chain, type A) (Nonmuscle myosin heavy chain-A) (NMMHC-A) |
| P51884 | 5 | Lumican precursor (Keratan sulfate proteoglycan lumican) (KSPG lumican) |
| P68366 | 5 | Tubulin alpha-1 chain (Alpha-tubulin 1) (Testis-specific alpha-tubulin) (Tubulin H2-alpha) |
| O15230 | 4 | Laminin alpha-5 chain precursor |
| P01922 | 4 | Hemoglobin alpha chain |
| P07951 | 4 | Tropomyosin beta chain (Tropomyosin 2) (Beta-tropomyosin) |
| P11047 | 4 | Laminin gamma-1 chain precursor (Laminin B2 chain) |
| P12277 | 4 | Creatine kinase, B chain (EC 2.7.3.2) (B-CK) |
| P20774 | 4 | Mimecan precursor (Osteoglycin) (Osteoinductive factor) (OIF) |
| P25705 | 4 | ATP synthase alpha chain, mitochondrial precursor (EC 3.6.3.14) |
| Q15598 | 4 | Titin (Fragment) |
| Q9Y490 | 4 | Talin 1 |
| O14558 | 3 | Heat-shock protein beta-6 (HspB6) (Heat-shock 20 kDa like-protein p20) |
| P01024 | 3 | Complement C3 precursor [Contains: C3a anaphylatoxin] |
| P01857 | 3 | Ig gamma-1 chain C region |
| P02144 | 3 | Myoglobin |
| P02452 | 3 | Collagen alpha 1(I) chain precursor |
| P02751 | 3 | Fibronectin precursor (FN) (Cold-insoluble globulin) (CIG) |
| P04075 | 3 | Fructose-bisphosphate aldolase A (EC 4.1.2.13) (Muscle-type aldolase) (Lung cancer antigen NY-LU-1) |
| P04083 | 3 | Annexin A1 (Annexin I) (Lipocortin I) (Calpactin II) (Chromobindin 9) (P35) (Phospholipase A2 inhibitory protein) |

TABLE 1-continued

| GenBank Accession | Number of Peptide analytes | Protein |
|---|---|---|
| P04406 | 3 | Glyceraldehyde-3-phosphate dehydrogenase, liver (EC 1.2.1.12) (GAPDH) |
| P06396 | 3 | Gelsolin precursor (Actin-depolymerizing factor) (ADF) (Brevin) (AGEL) |
| P06753 | 3 | Tropomyosin alpha 3 chain (Tropomyosin 3) (Tropomyosin gamma) (hTM5) |
| P08107 | 3 | Heat shock 70 kDa protein 1 (HSP70.1) (HSP70-1/HSP70-2) |
| P08123 | 3 | Collagen alpha 2(I) chain precursor |
| P08590 | 3 | Myosin light polypeptide 3 (Myosin light chain 1, slow-twitch muscle B/ventricular isoform) (MLC1SB) (Ventricular/slow twitch myosin alkali light chain) (Cardiac myosin light chain-1) (CMLC1) |
| P08758 | 3 | Annexin A5 (Annexin V) (Lipocortin V) (Endonexin II) (Calphobindin I) (CBP-I) (Placental anticoagulant protein I) (PAP-I) (PP4) (Thromboplastin inhibitor) (Vascular anticoagulant-alpha) (VAC-alpha) (Anchorin CII) |
| P11217 | 3 | Glycogen phosphorylase, muscle form (EC 2.4.1.1) (Myophosphorylase) |
| P13645 | 3 | Keratin, type I cytoskeletal 10 (Cytokeratin 10) (K10) (CK 10) |
| P14618 | 3 | Pyruvate kinase, isozymes M1/M2 (EC 2.7.1.40) (Pyruvate kinase muscle isozyme) (Cytosolic thyroid hormone-binding protein) (CTHBP) (THBP1) |
| P16615 | 3 | Sarcoplasmic/endoplasmic reticulum calcium ATPase 2 (EC 3.6.3.8) (Calcium pump 2) (SERCA2) (SR Ca(2+)-ATPase 2) (Calcium-transporting ATPase sarcoplasmic reticulum type, slow twitch skeletal muscle isoform) (Endoplasmic reticulum class 1/2 Ca(2+) ATPase) |
| P20929 | 3 | Nebulin |
| P28001 | 3 | Histone H2A.a (H2A/a) (H2A.2) |
| P51888 | 3 | Prolargin precursor (Proline-arginine-rich end leucine-rich repeat protein) |
| P60174 | 3 | Triosephosphate isomerase (EC 5.3.1.1) (TIM) (Triose-phosphate isomerase) |
| P60709 | 3 | Actin, cytoplasmic 1 (Beta-actin) |
| P62805 | 3 | Histone H4 |
| Q00872 | 3 | Myosin-binding protein C, slow-type (Slow MyBP-C) (C-protein, skeletal muscle slow-isoform) |
| Q05682 | 3 | Caldesmon (CDM) |
| Q15124 | 3 | Phosphoglucomutase-like protein 5 (Phosphoglucomutase-related protein) (PGM-RP) (Aciculin) |
| Q15149 | 3 | Plectin 1 (PLTN) (PCN) (Hemidesmosomal protein 1) (HD1) |
| Q15746 | 3 | Myosin light chain kinase, smooth muscle and non-muscle isozymes (EC 2.7.1.117) (MLCK) [Contains: Telokin (Kinase related protein) (KRP)] |
| Q6NZI2 | 3 | Polymerase I and transcript release factor (PTRF protein) (FKSG13 protein) |
| Q96C67 | 3 | COL14A1 protein |
| O14904 | 2 | Wnt-9a protein precursor (Wnt-14) |
| O14983 | 2 | Sarcoplasmic/endoplasmic reticulum calcium ATPase 1 (EC 3.6.3.8) (Calcium pump 1) (SERCA1) (SR Ca(2+)-ATPase 1) (Calcium-transporting ATPase sarcoplasmic reticulum type, fast twitch skeletal muscle isoform) (Endoplasmic reticulum class 1/2 Ca(2+) ATPase) |
| O95450 | 2 | ADAMTS-2 precursor (EC 3.4.24.14) (A disintegrin and metalloproteinase with thrombospondin motifs 2) (ADAM-TS 2) (ADAM-TS2) (Procollagen I/II amino-propeptide processing enzyme) (Procollagen I N-proteinase) (PC I-NP) (Procollagen N-endopeptidase) (pNPI) |
| O95613 | 2 | Pericentrin 2 (Pericentrin B) (Kendrin) |
| P00338 | 2 | L-lactate dehydrogenase A chain (EC 1.1.1.27) (LDH-A) (LDH muscle subunit) (LDH-M) |
| P01834 | 2 | Ig kappa chain C region |
| P01876 | 2 | Ig alpha-1 chain C region |
| P02511 | 2 | Alpha crystallin B chain (Alpha(B)-crystallin) (Rosenthal fiber component) (Heat-shock protein beta-5) (HspB5) |
| P02671 | 2 | Fibrinogen alpha/alpha-E chain precursor [Contains: Fibrinopeptide A] |
| P02766 | 2 | Transthyretin precursor (Prealbumin) (TBPA) (TTR) (ATTR) |
| P02787 | 2 | Serotransferrin precursor (Transferrin) (Siderophilin) (Beta-1-metal binding globulin) (PRO1400) |
| P04264 | 2 | Keratin, type II cytoskeletal 1 (Cytokeratin 1) (K1) (CK 1) (67 kDa cytokeratin) (Hair alpha protein) |
| P05787 | 2 | Keratin, type II cytoskeletal 8 (Cytokeratin 8) (K8) (CK 8) |
| P06702 | 2 | Calgranulin B (Migration inhibitory factor-related protein 14) (MRP-14) (P14) (Leukocyte L1 complex heavy chain) (S100 calcium-binding protein A9) (Calprotectin L1H subunit) |
| P07451 | 2 | Carbonic anhydrase III (EC 4.2.1.1) (Carbonate dehydratase III) (CA-III) |
| P07737 | 2 | Profilin-1 (Profilin I) |
| P08133 | 2 | Annexin A6 (Annexin VI) (Lipocortin VI) (P68) (P70) (Protein III) (Chromobindin 20) (67 kDa calelectrin) (Calphobindin-II) (CPB-II) |
| P10916 | 2 | Myosin regulatory light chain 2, ventricular/cardiac muscle isoform (MLC-2) (MLC-2v) |
| P14649 | 2 | Myosin light chain 1, slow-twitch muscle A isoform (MLC1sa) (Alkali) |
| P17174 | 2 | Aspartate aminotransferase, cytoplasmic (EC 2.6.1.1) (Transaminase A) (Glutamate oxaloacetate transaminase-1) |
| P17540 | 2 | Creatine kinase, sarcomeric mitochondrial precursor (EC 2.7.3.2) (S-MtCK) (Mib-CK) (Basic-type mitochondrial creatine kinase) |
| P21810 | 2 | Biglycan precursor (Bone/cartilage proteoglycan I) (PG-S1) |
| P24844 | 2 | Myosin regulatory light chain 2, smooth muscle isoform (Myosin RLC) (LC20) |
| P29536 | 2 | Leiomodin 1 (Leiomodin, muscle form) (64 kDa autoantigen D1) (64 kDa autoantigen 1D) (64 kDa autoantigen 1D3) (Thyroid-associated ophthalmopathy autoantigen) (Smooth muscle leiomodin) (SM-Lmod) |

TABLE 1-continued

| GenBank Accession | Number of Peptide analytes | Protein |
|---|---|---|
| P35555 | 2 | Fibrillin 1 precursor |
| P35580 | 2 | Myosin heavy chain, nonmuscle type B (Cellular myosin heavy chain, type B) (Nonmuscle myosin heavy chain-B) (NMMHC-B) |
| P40925 | 2 | Malate dehydrogenase, cytoplasmic (EC 1.1.1.37) |
| P51911 | 2 | Calponin 1 (Calponin H1, smooth muscle) (Basic calponin) |
| P54652 | 2 | Heat shock-related 70 kDa protein 2 (Heat shock 70 kDa protein 2) |
| P63316 | 2 | Troponin C, slow skeletal and cardiac muscles (TN-C) |
| P68133 | 2 | Actin, alpha skeletal muscle (Alpha-actin 1) |
| P68371 | 2 | Tubulin beta-2 chain |
| Q02952 | 2 | A-kinase anchor protein 12 (A-kinase anchor protein 250 kDa) (AKAP 250) (Myasthenia gravis autoantigen gravin) |
| Q09666 | 2 | Neuroblast differentiation associated protein AHNAK (Desmoyokin) (Fragments) |
| Q10465 | 2 | Elastic titin (Fragment) |
| Q13017 | 2 | Rho-GTPase-activating protein 5 (p190-B) |
| Q13642 | 2 | Skeletal muscle LIM-protein 1 (SLIM 1) (SLIM) (Four and a half LIM domains protein 1) (FHL-1) |
| Q13748 | 2 | Tubulin alpha-2 chain (Alpha-tubulin 2) |
| Q14112 | 2 | Nidogen-2 precursor (NID-2) (Osteonidogen) |
| Q14843 | 2 | Myosin light chain 2 |
| Q15582 | 2 | Transforming growth factor-beta induced protein IG-H3 precursor (Beta IG-H3) (Kerato-epithelin) (RGD-containing collagen associated protein) (RGD-CAP) |
| Q16659 | 2 | Mitogen-activated protein kinase 6 (EC 2.7.1.37) (Extracellular signal-regulated kinase 3) (ERK-3) (MAP kinase isoform p97) (p97-MAPK) |
| Q6DV90 | 2 | Sarcomeric tropomyosin kappa |
| Q6P0Q1 | 2 | Alpha 2 type VI collagen, isoform 2C2 |
| Q96RL7 | 2 | Vacuolar protein sorting 13A (Chorein) (Chorea-acanthocytosis protein) |
| Q9BVJ6 | 2 | UTP14, U3 small nucleolar ribonucleoprotein, homolog A |
| Q9BX66 | 2 | Sorbin and SH3 domain-containing protein 1 (Ponsin) (c-Cbl-associated protein) (CAP) (SH3 domain protein 5) (SH3P12) |
| Q9NQ75 | 2 | HEF-like protein2 |
| Q9NZN4 | 2 | EH-domain containing protein 2 |
| Q9Y4Z4 | 2 | ZASP protein (Fragment) |
| O00232 | 1 | 26S proteasome non-ATPase regulatory subunit 12 (26S proteasome regulatory subunit p55) |
| O00260 | 1 | Collagen type XIV precursor (Fragment) |
| O00281 | 1 | D9 splice variant A |
| O00295 | 1 | Tubby related protein 2 (Tubby-like protein 2) |
| O00321 | 1 | Ets translocation variant 2 (Ets-related protein 71) |
| O00555 | 1 | Voltage-dependent P/Q-type calcium channel alpha-1A subunit (Voltage-gated calcium channel alpha subunit Cav2.1) (Calcium channel, L type, alpha-1 polypeptide isoform 4) (Brain calcium channel I) (BI) |
| O14497 | 1 | SWI/SNF-related, matrix-associated, actin-dependent regulator of chromatin subfamily F member 1 (SWI-SNF complex protein p270) (B120) |
| O14877 | 1 | FrpHE |
| O14958 | 1 | Calsequestrin, cardiac muscle isoform precursor (Calsequestrin 2) |
| O15025 | 1 | KIAA0308 protein (Fragment) |
| O15463 | 1 | PTPL1-associated RhoGAP |
| O15527 | 1 | N-glycosylase/DNA lyase [Includes: 8-oxoguanine DNA glycosylase (EC 3.2.2.—); DNA-(apurinic or apyrimidinic site) lyase (EC 4.2.99.18) (AP lyase)] |
| O43167 | 1 | Zinc finger and BTB domain containing protein 24 (Zinc finger protein 450) |
| O43174 | 1 | Cytochrome P450 26 (EC 1.14.—.—) (Retinoic acid-metabolizing cytochrome) (P450 retinoic acid-inactivating 1) (P450RAI) (hP450RAI) (Retinoic acid 4-hydroxylase) |
| O43316 | 1 | Paired box protein Pax-4 |
| O43707 | 1 | Alpha-actinin 4 (Non-muscle alpha-actinin 4) (F-actin cross linking protein) |
| O60231 | 1 | Putative pre-mRNA splicing factor RNA helicase (ATP-dependent RNA helicase #3) (DEAH-box protein 16) |
| O60232 | 1 | Sjogren's syndrome/scleroderma autoantigen 1 (Autoantigen p27) |
| O60279 | 1 | KIAA0527 protein (Fragment) |
| O60423 | 1 | Potential phospholipid-transporting ATPase IK (EC 3.6.3.1) (ATPase class I type 8B member 3) |
| O60488 | 1 | Long-chain-fatty-acid--CoA ligase 4 (EC 6.2.1.3) (Long-chain acyl-CoA synthetase 4) (LACS 4) |
| O60662 | 1 | Kelch repeat and BTB domain containing protein 10 (Kelch-related protein 1) (Kel-like protein 23) (Sarcosin) |
| O75019 | 1 | Leukocyte immunoglobulin-like receptor subfamily A member 1 precursor (Leucocyte immunoglobulin-like receptor 6) (LIR-6) (CD85i antigen) |
| O75039 | 1 | KIAA0451 protein (Fragment) |
| O75128 | 1 | KIAA0633 protein (Fragment) |
| O75147 | 1 | KIAA0657 protein (Fragment) |
| O75369 | 1 | Filamin B (FLN-B) (Beta-filamin) (Actin-binding like protein) (Thyroid autoantigen) (Truncated actin-binding protein) (Truncated ABP) (ABP-280 homolog) (ABP-278) (Filamin 3) (Filamin homolog 1) (Fh1) |
| O75373 | 1 | Zinc finger protein (Fragment) |
| O75477 | 1 | KE04p (Chromosome 10 open reading frame 69) (Novel protein) (FLJ32012) |

TABLE 1-continued

| GenBank Accession | Number of Peptide analytes | Protein |
|---|---|---|
| O75643 | 1 | U5 small nuclear ribonucleoprotein 200 kDa helicase (EC 3.6.1.—) (U5 snRNP-specific 200 kDa protein) (U5-200KD) (Activating signal cointegrator 1 complex subunit 3-like 1) |
| O75691 | 1 | DRIM protein |
| O75701 | 1 | Hypothetical protein A-635H12.2 |
| O75797 | 1 | ORF-2 |
| O75822 | 1 | Eukaryotic translation initiation factor 3 subunit 1 (eIF-3 alpha) (eIF3 p35) (eIF3j) |
| O75828 | 1 | Carbonyl reductase [NADPH] 3 (EC 1.1.1.184) (NADPH-dependent carbonyl reductase 3) |
| O75891 | 1 | 10-formyltetrahydrofolate dehydrogenase (EC 1.5.1.6) (10-FTHFDH) |
| O75912 | 1 | Diacylglycerol kinase, iota (EC 2.7.1.107) (Diglyceride kinase) (DGK-iota) (DAG kinase iota) |
| O76064 | 1 | Ubiquitin ligase protein RNF8 (EC 6.3.2.—) (RING finger protein 8) |
| O94788 | 1 | Aldehyde dehydrogenase 1A2 (EC 1.2.1.3) (Retinaldehyde-specific dehydrogenase type 2) (RALDH(II)) (RALDH-2) |
| O94807 | 1 | Telomerase transcriptase (Fragment) |
| O94818 | 1 | Nucleolar protein 4 (Nucleolar-localized protein) (HRIHFB2255) |
| O94819 | 1 | Protein KIAA0711 |
| O94851 | 1 | Protein MICAL-2 |
| O94863 | 1 | KIAA0763 protein (Fragment) |
| O94921 | 1 | Serine/threonine-protein kinase PFTAIRE-1 (EC 2.7.1.37) |
| O94936 | 1 | KIAA0853 protein (Fragment) |
| O95153 | 1 | Peripheral-type benzodiazepine receptor-associated protein 1 (PRAX-1) (Peripheral benzodiazepine receptor interacting protein) (PBR-IP) (RIM binding protein 1) (RIM-BP1) |
| O95185 | 1 | Netrin receptor UNC5C precursor (Unc-5 homolog C) (Unc-5 homolog 3) |
| O95218 | 1 | Zinc finger protein 265 (Zinc finger, splicing) |
| O95477 | 1 | ATP-binding cassette, sub-family A, member 1 (ATP-binding cassette transporter 1) (ATP-binding cassette 1) (ABC-1) (Cholesterol efflux regulatory protein) |
| O95704 | 1 | Amyloid beta A4 precursor protein-binding family B member 3 (Fe65-like protein 2) (Fe65L2) |
| O95714 | 1 | HERC2 protein |
| O95872 | 1 | Protein BAT4 (HLA-B-associated transcript 4) (G5) |
| P00352 | 1 | Aldehyde dehydrogenase 1A1 (EC 1.2.1.3) (Aldehyde dehydrogenase, cytosolic) (ALDH class 1) (Retinal dehydrogenase 1) (ALHDII) (ALDH-E1) |
| P00354 | 1 | Glyceraldehyde-3-phosphate dehydrogenase, muscle (EC 1.2.1.12) (GAPDH) |
| P00441 | 1 | Superoxide dismutase [Cu—Zn] (EC 1.15.1.1) |
| P00450 | 1 | Ceruloplasmin precursor (EC 1.16.3.1) (Ferroxidase) |
| P00747 | 1 | Plasminogen precursor (EC 3.4.21.7) [Contains: Angiostatin] |
| P01009 | 1 | Alpha-1-antitrypsin precursor (Alpha-1 protease inhibitor) (Alpha-1-antiproteinase) (PRO0684/PRO2209) |
| P01023 | 1 | Alpha-2-macroglobulin precursor (Alpha-2-M) |
| P01028 | 1 | Complement C4 precursor [Contains: C4a anaphylatoxin; C4b] |
| P01620 | 1 | Ig kappa chain V-III region SIE |
| P01737 | 1 | T-cell receptor alpha chain V region PY14 precursor |
| P01765 | 1 | Ig heavy chain V-III region TIL |
| P01780 | 1 | Ig heavy chain V-III region JON |
| P01842 | 1 | Ig lambda chain C regions |
| P02042 | 1 | Hemoglobin delta chain |
| P02461 | 1 | Collagen alpha 1(III) chain precursor |
| P02533 | 1 | Keratin, type I cytoskeletal 14 (Cytokeratin 14) (K14) (CK 14) |
| P02585 | 1 | Troponin C, skeletal muscle |
| P02679 | 1 | Fibrinogen gamma chain precursor (PRO2061) |
| P02760 | 1 | AMBP protein precursor [Contains: Alpha-1-microglobulin (Protein HC) (Complex-forming glycoprotein heterogeneous in charge) (Alpha-1 microglycoprotein); Inter-alpha-trypsin inhibitor light chain (ITI-LC) (Bikunin) (HI-30)] |
| P02790 | 1 | Hemopexin precursor (Beta-1B-glycoprotein) |
| P02792 | 1 | Ferritin light chain (Ferritin L subunit) |
| P04004 | 1 | Vitronectin precursor (Serum spreading factor) (S-protein) (V75) [Contains: Vitronectin V65 subunit; Vitronectin V10 subunit; Somatomedin B] |
| P04179 | 1 | Superoxide dismutase [Mn], mitochondrial precursor (EC 1.15.1.1) |
| P04196 | 1 | Histidine-rich glycoprotein precursor (Histidine-proline rich glycoprotein) (HPRG) |
| P04220 | 1 | Ig mu heavy chain disease protein (BOT) |
| P05155 | 1 | Plasma protease C1 inhibitor precursor (C1 Inh) (C1Inh) |
| P06733 | 1 | Alpha enolase (EC 4.2.1.11) (2-phospho-D-glycerate hydro-lyase) (Non-neural enolase) (NNE) (Enolase 1) (Phosphopyruvate hydratase) (C-myc promoter-binding protein) (MBP-1) (MPB-1) (Plasminogen-binding protein) |
| P06737 | 1 | Glycogen phosphorylase, liver form (EC 2.4.1.1) |
| P06744 | 1 | Glucose-6-phosphate isomerase (EC 5.3.1.9) (GPI) (Phosphoglucose isomerase) (PGI) (Phosphohexose isomerase) (PHI) (Neuroleukin) (NLK) (Sperm antigen-36) (SA-36) |
| P07195 | 1 | L-lactate dehydrogenase B chain (EC 1.1.1.27) (LDH-B) (LDH heart subunit) (LDH-H) |
| P07288 | 1 | Prostate specific antigen precursor (EC 3.4.21.77) (PSA) (Gamma-seminoprotein) (Kallikrein 3) (Semenogelase) (Seminin) (P-30 antigen) |
| P07358 | 1 | Complement component C8 beta chain precursor |
| P07602 | 1 | Proactivator polypeptide precursor [Contains: Saposin A (Protein A); Saposin B (Sphingolipid activator protein 1) (SAP-1) (Cerebroside sulfate activator) (CSAct) |

TABLE 1-continued

| GenBank Accession | Number of Peptide analytes | Protein |
|---|---|---|
| | | (Dispersin) (Sulfatide/GM1 activator); Saposin C (Co-beta-glucosidase) (A1 activator) (Glucos |
| P07900 | 1 | Heat shock protein HSP 90-alpha (HSP 86) |
| P08238 | 1 | Heat shock protein HSP 90-beta (HSP 84) (HSP 90) |
| P08572 | 1 | Collagen alpha 2(IV) chain precursor |
| P09211 | 1 | Glutathione S-transferase P (EC 2.5.1.18) (GST class-pi) (GSTP1-1) |
| P09382 | 1 | Galectin-1 (Beta-galactoside-binding lectin L-14-I) (Lactose-binding lectin 1) (S-Lac lectin 1) (Galaptin) (14 kDa lectin) (HPL) (HBL) |
| P09488 | 1 | Glutathione S-transferase Mu 1 (EC 2.5.1.18) (GSTM1-1) (GST class-mu 1) (GSTM1a-1a) (GSTM1b-1b) (HB subunit 4) (GTH4) |
| P09525 | 1 | Annexin A4 (Annexin IV) (Lipocortin IV) (Endonexin I) (Chromobindin 4) (Protein II) (P32.5) (Placental anticoagulant protein II) (PAP-II) (PP4-X) (35-beta calcimedin) (Carbohydrate-binding protein P33/P41) (P33/41) |
| P09543 | 1 | 2',3'-cyclic-nucleotide 3'-phosphodiesterase (EC 3.1.4.37) (CNP) (CNPase) |
| P09913 | 1 | Interferon-induced protein with tetratricopeptide repeats 2 (IFIT-2) (Interferon-induced 54 kDa protein) (IFI-54K) (ISG-54 K) |
| P09972 | 1 | Fructose-bisphosphate aldolase C (EC 4.1.2.13) (Brain-type aldolase) |
| P10155 | 1 | 60-kDa SS-A/Ro ribonucleoprotein (60 kDa Ro protein) (60 kDa ribonucleoprotein Ro) (RoRNP) (Ro 60 kDa autoantigen) (Sjogren syndrome type A antigen) (SS-A) (Sjogren syndrome antigen A2) |
| P10909 | 1 | Clusterin precursor (Complement-associated protein SP-40,40) (Complement cytolysis inhibitor) (CLI) (NA1/NA2) (Apolipoprotein J) (Apo-J) (Testosterone-repressed prostate message 2) (TRPM-2) |
| P11021 | 1 | 78 kDa glucose-regulated protein precursor (GRP 78) (Immunoglobulin heavy chain binding protein) (BiP) (Endoplasmic reticulum lumenal Ca(2+) binding protein grp78) |
| P11055 | 1 | Myosin heavy chain, fast skeletal muscle, embryonic (Muscle embryonic myosin heavy chain) (SMHCE) |
| P11142 | 1 | Heat shock cognate 71 kDa protein (Heat shock 70 kDa protein 8) |
| P11474 | 1 | Steroid hormone receptor ERR1 (Estrogen-related receptor, alpha) (ERR-alpha) (Estrogen receptor-like 1) |
| P11498 | 1 | Pyruvate carboxylase, mitochondrial precursor (EC 6.4.1.1) (Pyruvic carboxylase) (PCB) |
| P12273 | 1 | Prolactin-inducible protein precursor (Secretory actin-binding protein) (SABP) (Gross cystic disease fluid protein 15) (GCDFP-15) (gp17) |
| P13646 | 1 | Keratin, type I cytoskeletal 13 (Cytokeratin 13) (K13) (CK 13) |
| P13647 | 1 | Keratin, type II cytoskeletal 5 (Cytokeratin 5) (K5) (CK 5) (58 kDa cytokeratin) |
| P13805 | 1 | Troponin T, slow skeletal muscle isoforms (Slow skeletal muscle troponin T) |
| P13945 | 1 | Beta-3 adrenergic receptor (Beta-3 adrenoceptor) (Beta-3 adrenoreceptor) |
| P14543 | 1 | Nidogen precursor (Entactin) |
| P14550 | 1 | Alcohol dehydrogenase [NADP+] (EC 1.1.1.2) (Aldehyde reductase) (Aldo-keto reductase family 1 member A1) |
| P15311 | 1 | Ezrin (p81) (Cytovillin) (Villin 2) |
| P15822 | 1 | Zinc finger protein 40 (Human immunodeficiency virus type I enhancer-binding protein 1) (HIV-EP1) (Major histocompatibility complex binding protein 1) (MBP-1) (Positive regulatory domain II binding factor 1) (PRDII-BF1) |
| P15976 | 1 | Erythroid transcription factor (GATA-1) (Eryf1) (GF-1) (NF-E1) |
| P16066 | 1 | Atrial natriuretic peptide receptor A precursor (ANP-A) (ANPRA) (GC-A) (Guanylate cyclase) (EC 4.6.1.2) (NPR-A) (Atrial natriuretic peptide A-type receptor) |
| P16415 | 1 | Zinc finger protein ZFP-36 (Fragment) |
| P17483 | 1 | Homeobox protein Hox-B4 (Hox-2F) (Hox-2.6) |
| P18054 | 1 | Arachidonate 12-lipoxygenase, 12S-type (EC 1.13.11.31) (12-LOX) (Platelet-type lipoxygenase 12) |
| P18669 | 1 | Phosphoglycerate mutase 1 (EC 5.4.2.1) (EC 5.4.2.4) (EC 3.1.3.13) (Phosphoglycerate mutase isozyme B) (PGAM-B) (BPG-dependent PGAM 1) |
| P19022 | 1 | Neural-cadherin precursor (N-cadherin) (Cadherin-2) |
| P19105 | 1 | Myosin regulatory light chain 2, nonsarcomeric (Myosin RLC) |
| P19784 | 1 | Casein kinase II, alpha' chain (CK II) (EC 2.7.1.37) |
| P19835 | 1 | Bile-salt-activated lipase precursor (EC 3.1.1.3) (EC 3.1.1.13) (BAL) (Bile-salt-stimulated lipase) (BSSL) (Carboxyl ester lipase) (Sterol esterase) (Cholesterol esterase) (Pancreatic lysophospholipase) |
| P20073 | 1 | Annexin A7 (Annexin VII) (Synexin) (OK/SW-cl.95) |
| P20231 | 1 | Tryptase beta-2 precursor (EC 3.4.21.59) (Tryptase 2) (Tryptase II) |
| P20339 | 1 | Ras-related protein Rab-5A |
| P20908 | 1 | Collagen alpha 1(V) chain precursor |
| P21266 | 1 | Glutathione S-transferase Mu 3 (EC 2.5.1.18) (GSTM3-3) (GST class-mu 3) (hGSTM3-3) |
| P21291 | 1 | Cysteine and glycine-rich protein 1 (Cysteine-rich protein 1) (CRP1) (CRP) |
| P21359 | 1 | Neurofibromin (Neurofibromatosis-related protein NF-1) [Contains: Neurofibromin truncated] |
| P21817 | 1 | Ryanodine receptor 1 (Skeletal muscle-type ryanodine receptor) (RyR1) (RYR-1) (Skeletal muscle calcium release channel) |
| P22079 | 1 | Lactoperoxidase precursor (EC 1.11.1.7) (LPO) (Salivary peroxidase) (SPO) |
| P22695 | 1 | Ubiquinol-cytochrome-c reductase complex core protein 2, mitochondrial precursor (EC 1.10.2.2) (Complex III subunit II) |
| P23142 | 1 | Fibulin-1 precursor |
| P23468 | 1 | Receptor-type tyrosine-protein phosphatase delta precursor (EC 3.1.3.48) (Protein-tyrosine phosphatase delta) (R-PTP-delta) |

TABLE 1-continued

| GenBank Accession | Number of Peptide analytes | Protein |
|---|---|---|
| P23528 | 1 | Cofilin, non-muscle isoform (Cofilin-1) (18 kDa phosphoprotein) (p18) |
| P24752 | 1 | Acetyl-CoA acetyltransferase, mitochondrial precursor (EC 2.3.1.9) (Acetoacetyl-CoA thiolase) (T2) |
| P25100 | 1 | Alpha-1D adrenergic receptor (Alpha 1D-adrenoceptor) (Alpha 1D-adrenoreceptor) (Alpha-1A adrenergic receptor) (Alpha adrenergic receptor 1a) |
| P25311 | 1 | Zinc-alpha-2-glycoprotein precursor (Zn-alpha-2-glycoprotein) (Zn-alpha-2-GP) |
| P25940 | 1 | Collagen alpha 3(V) chain precursor |
| P26196 | 1 | Probable ATP-dependent RNA helicase p54 (Oncogene RCK) (DEAD-box protein 6) |
| P26640 | 1 | Valyl-tRNA synthetase 2 (EC 6.1.1.9) (Valine--tRNA ligase 2) (ValRS 2) (G7a) |
| P27105 | 1 | Erythrocyte band 7 integral membrane protein (Stomatin) (Protein 7.2b) |
| P27708 | 1 | CAD protein [Includes: Glutamine-dependent carbamoyl-phosphate synthase (EC 6.3.5.5); Aspartate carbamoyltransferase (EC 2.1.3.2); Dihydroorotase (EC 3.5.2.3)] |
| P27824 | 1 | Calnexin precursor (Major histocompatibility complex class I antigen-binding protein p88) (p90) (IP90) |
| P27986 | 1 | Phosphatidylinositol 3-kinase regulatory alpha subunit (PI3-kinase p85-alpha subunit) (PtdIns-3-kinase p85-alpha) (PI3K) |
| P28289 | 1 | Tropomodulin 1 (Erythrocyte tropomodulin) (E-Tmod) |
| P28331 | 1 | NADH-ubiquinone oxidoreductase 75 kDa subunit, mitochondrial precursor (EC 1.6.5.3) (EC 1.6.99.3) (Complex I-75Kd) (CI-75Kd) |
| P28749 | 1 | Retinoblastoma-like protein 1 (107 kDa retinoblastoma-associated protein) (PRB1) (P107) |
| P30041 | 1 | Peroxiredoxin 6 (EC 1.11.1.—) (Antioxidant protein 2) (1-Cys peroxiredoxin) (1-Cys PRX) (Acidic calcium-independent phospholipase A2) (EC 3.1.1.—) (aiPLA2) (Non-selenium glutathione peroxidase) (EC 1.11.1.7) (NSGPx) (24 kDa protein) (Liver 2D page spot 40 |
| P30048 | 1 | Thioredoxin-dependent peroxide reductase, mitochondrial precursor (EC 1.11.1.—) (Peroxiredoxin 3) (Antioxidant protein 1) (AOP-1) (MER5 protein homolog) (HBC189) (PRX III) |
| P30049 | 1 | ATP synthase delta chain, mitochondrial precursor (EC 3.6.3.14) |
| P30085 | 1 | UMP-CMP kinase (EC 2.7.4.14) (Cytidylate kinase) (Deoxycytidylate kinase) (Cytidine monophosphate kinase) |
| P30086 | 1 | Phosphatidylethanolamine-binding protein (PEBP) (Prostatic binding protein) (HCNPpp) (Neuropolypeptide h3) (Raf kinase inhibitor protein) (RKIP) [Contains: Hippocampal cholinergic neurostimulating peptide (HCNP)] |
| P30101 | 1 | Protein disulfide-isomerase A3 precursor (EC 5.3.4.1) (Disulfide isomerase ER-60) (ERp60) (58 kDa microsomal protein) (p58) (ERp57) (58 kDa glucose regulated protein) |
| P30443 | 1 | HLA class I histocompatibility antigen, A-1 alpha chain precursor (MHC class I antigen A*1) |
| P30518 | 1 | Vasopressin V2 receptor (Renal-type arginine vasopressin receptor) (Antidiuretic hormone receptor) (AVPR V2) |
| P30530 | 1 | Tyrosine-protein kinase receptor UFO precursor (EC 2.7.1.112) (AXL oncogene) |
| P30532 | 1 | Neuronal acetylcholine receptor protein, alpha-5 chain precursor |
| P30712 | 1 | Glutathione S-transferase theta 2 (EC 2.5.1.18) (GST class-theta 2) |
| P30837 | 1 | Aldehyde dehydrogenase X, mitochondrial precursor (EC 1.2.1.3) (ALDH class 2) |
| P31025 | 1 | Von Ebner's gland protein precursor (VEG protein) (Tear prealbumin) (TP) (Tear lipocalin) (Lipocalin 1) |
| P31040 | 1 | Succinate dehydrogenase [ubiquinone] flavoprotein subunit, mitochondrial precursor (EC 1.3.5.1) (Fp) (Flavoprotein subunit of complex II) |
| P31150 | 1 | Rab GDP dissociation inhibitor alpha (Rab GDI alpha) (GDI-1) (XAP-4) (Oligophrenin 2) |
| P31323 | 1 | cAMP-dependent protein kinase type II-beta regulatory subunit |
| P32119 | 1 | Peroxiredoxin 2 (EC 1.11.1.—) (Thioredoxin peroxidase 1) (Thioredoxin-dependent peroxide reductase 1) (Thiol-specific antioxidant protein) (TSA) (PRP) (Natural killer cell enhancing factor B) (NKEF-B) |
| P32242 | 1 | Homeobox protein OTX1 |
| P32243 | 1 | Homeobox protein OTX2 |
| P33981 | 1 | Dual specificity protein kinase TTK (EC 2.7.1.—) (Phosphotyrosine picked threonine kinase) (PYT) |
| P35030 | 1 | Trypsin III precursor (EC 3.4.21.4) (Brain trypsinogen) (Mesotrypsinogen) (Trypsin IV) |
| P35237 | 1 | Placental thrombin inhibitor (Cytoplasmic antiproteinase) (CAP) (Protease inhibitor 6) (PI-6) |
| P35270 | 1 | Sepiapterin reductase (EC 1.1.1.153) (SPR) |
| P35527 | 1 | Keratin, type I cytoskeletal 9 (Cytokeratin 9) (K9) (CK 9) |
| P35908 | 1 | Keratin, type II cytoskeletal 2 epidermal (Cytokeratin 2e) (K2e) (CK 2e) |
| P36542 | 1 | ATP synthase gamma chain, mitochondrial precursor (EC 3.6.3.14) |
| P37802 | 1 | Transgelin-2 (SM22-alpha homolog) |
| P39059 | 1 | Collagen alpha 1(XV) chain precursor |
| P39060 | 1 | Collagen alpha 1(XVIII) chain precursor [Contains: Endostatin] |
| P40225 | 1 | Thrombopoietin precursor (Megakaryocyte colony stimulating factor) (Myeloproliferative leukemia virus oncogene ligand) (C-mpl ligand) (ML) (Megakaryocyte growth and development factor) (MGDF) |
| P40818 | 1 | Ubiquitin carboxyl-terminal hydrolase 8 (EC 3.1.2.15) (Ubiquitin thiolesterase 8) (Ubiquitin-specific processing protease 8) (Deubiquitinating enzyme 8) (hUBPy) |
| P40939 | 1 | Trifunctional enzyme alpha subunit, mitochondrial precursor (TP-alpha) (78 kDa gastrin-binding protein) [Includes: Long-chain enoyl-CoA hydratase (EC 4.2.1.17); Long chain 3-hydroxyacyl-CoA dehydrogenase (EC 1.1.1.35)] |
| P41219 | 1 | Peripherin |
| P42331 | 1 | Rho-GTPase-activating protein 25 |

TABLE 1-continued

| GenBank Accession | Number of Peptide analytes | Protein |
|---|---|---|
| P42357 | 1 | Histidine ammonia-lyase (EC 4.3.1.3) (Histidase) |
| P42658 | 1 | Dipeptidyl aminopeptidase-like protein 6 (Dipeptidylpeptidase VI) (Dipeptidylpeptidase 6) (Dipeptidyl peptidase IV like protein) (Dipeptidyl aminopeptidase-related protein) (DPPX) |
| P43155 | 1 | Carnitine O-acetyltransferase (EC 2.3.1.7) (Carnitine acetylase) (CAT) |
| P43250 | 1 | G protein-coupled receptor kinase 6 (EC 2.7.1.—) (G protein-coupled receptor kinase GRK6) |
| P48066 | 1 | Sodium- and chloride-dependent GABA transporter 3 |
| P48740 | 1 | Complement-activating component of Ra-reactive factor precursor (EC 3.4.21.—) (Ra-reactive factor serine protease p100) (RaRF) (Mannan-binding lectin serine protease 1) (Mannose-binding protein associated serine protease) (MASP-1) |
| P48995 | 1 | Short transient receptor potential channel 1 (TrpC1) (TRP-1 protein) |
| P49247 | 1 | Ribose-5-phosphate isomerase (EC 5.3.1.6) (Phosphoriboisomerase) |
| P49454 | 1 | CENP-F kinetochore protein (Centromere protein F) (Mitosin) (AH antigen) |
| P49746 | 1 | Thrombospondin 3 precursor |
| P49748 | 1 | Acyl-CoA dehydrogenase, very-long-chain specific, mitochondrial precursor (EC 1.3.99.—) (VLCAD) |
| P50461 | 1 | Cysteine and glycine-rich protein 3 (Cysteine-rich protein 3) (CRP3) (LIM domain protein, cardiac) (Muscle LIM protein) |
| P51530 | 1 | DNA2-like homolog (DNA replication helicase-like homolog) (Fragment) |
| P51531 | 1 | Possible global transcription activator SNF2L2 (SNF2-alpha) (SWI/SNF related matrix associated actin dependent regulator of chromatin subfamily A member 2) |
| P51610 | 1 | Host cell factor C1 (HCF) (VP16 accessory protein) (HFC1) (VCAF) (CFF) |
| P51828 | 1 | Adenylate cyclase, type VII (EC 4.6.1.1) (ATP pyrophosphate-lyase 7) (Adenylyl cyclase 7) |
| P52179 | 1 | Myomesin 1 (190 kDa titin-associated protein) (190 kDa connectin-associated protein) |
| P52306 | 1 | Rap1 GTPase-GDP dissociation stimulator 1 (SMG P21 stimulatory GDP/GTP exchange protein) (SMG GDS protein) (Exchange factor smgGDS) |
| P52799 | 1 | Ephrin-B2 precursor (EPH-related receptor tyrosine kinase ligand 5) (LERK-5) (HTK ligand) (HTK-L) |
| P52907 | 1 | F-actin capping protein alpha-1 subunit (CapZ alpha-1) |
| P53007 | 1 | Tricarboxylate transport protein, mitochondrial precursor (Citrate transport protein) (CTP) (Tricarboxylate carrier protein) |
| P53671 | 1 | LIM domain kinase 2 (EC 2.7.1.—) (LIMK-2) |
| P54296 | 1 | Myomesin 2 (M-protein) (165 kDa titin-associated protein) (165 kDa connectin-associated protein) |
| P55073 | 1 | Type III iodothyronine deiodinase (EC 1.97.1.11) (Type-III 5'deiodinase) (DIOIII) (Type 3 DI) (5DIII) |
| P55083 | 1 | Microfibril-associated glycoprotein 4 precursor |
| P55786 | 1 | Puromycin-sensitive aminopeptidase (EC 3.4.11.—) (PSA) |
| P55854 | 1 | Ubiquitin-like protein SMT3A |
| P56704 | 1 | Wnt-3a protein precursor |
| P58658 | 1 | Protein C21orf63 precursor (Protein PRED34) (SUE21) (UNQ2504/PRO5993) |
| P60323 | 1 | Nanos homolog 3 |
| P60413 | 1 | Keratin-associated protein 10-12 (Keratin-associated protein 10.12) (High sulfur keratin-associated protein 10.12) (Keratin-associated protein KAP18-12) (Keratin-associated protein 18.12) |
| P60660 | 1 | Myosin light polypeptide 6 (Myosin light chain alkali 3) (Myosin light chain 3) (MLC-3) (LC17) |
| P60981 | 1 | Destrin (Actin-depolymerizing factor) (ADF) |
| P61158 | 1 | Actin-like protein 3 (Actin-related protein 3) |
| P61764 | 1 | Syntaxin binding protein 1 (Unc-18 homolog) (Unc-18A) (Unc-18-1) (N-Sec1) (p67) |
| P61978 | 1 | Heterogeneous nuclear ribonucleoprotein K (hnRNP K) (Transformation up-regulated nuclear protein) (TUNP) |
| P61981 | 1 | 14-3-3 protein gamma (Protein kinase C inhibitor protein-1) (KCIP-1) |
| P62258 | 1 | 14-3-3 protein epsilon (14-3-3E) |
| P62341 | 1 | Selenoprotein T precursor (UNQ150/PRO176) |
| P62807 | 1 | Histone H2B.a/g/h/k/l (H2B.1 A) (H2B/a) (H2B/g) (H2B/h) (H2B/k) (H2B/l) |
| P62834 | 1 | Ras-related protein Rap-1A (GTP-binding protein smg-p21A) (Ras-related protein Krev-1) (C21KG) (G-22K) |
| P62988 | 1 | Ubiquitin |
| P63104 | 1 | 14-3-3 protein zeta/delta (Protein kinase C inhibitor protein-1) (KCIP-1) |
| P69891 | 1 | Hemoglobin gamma-1 chain (Hemoglobin gamma-A chain) (Hb F Agamma) |
| P78333 | 1 | Glypican-5 precursor |
| P78527 | 1 | DNA-dependent protein kinase catalytic subunit (EC 2.7.1.37) (DNA-PKcs) (DNPK1) (p460) |
| P82279 | 1 | Crumbs protein homolog 1 precursor |
| P98095 | 1 | Fibulin-2 precursor |
| P98161 | 1 | Polycystin 1 precursor (Autosomal dominant polycystic kidney disease protein 1) |
| P98194 | 1 | Calcium-transporting ATPase type 2C, member 1 (EC 3.6.3.8) (ATPase 2C1) (ATP-dependent Ca(2+) pump PMR1) (HUSSY-28) |
| Q00653 | 1 | Nuclear factor NF-kappa-B p100/p49 subunits (DNA-binding factor KBF2) (H2TF1) (Lymphocyte translocation chromosome 10) (Oncogene Lyt-10) (Lyt10) [Contains: Nuclear factor NF-kappa-B p52 subunit] |
| Q00839 | 1 | Heterogenous nuclear ribonucleoprotein U (hnRNP U) (Scaffold attachment factor A) (SAF-A) (pp120) |

TABLE 1-continued

| GenBank Accession | Number of Peptide analytes | Protein |
|---|---|---|
| Q01082 | 1 | Spectrin beta chain, brain 1 (Spectrin, non-erythroid beta chain 1) (Beta-II spectrin) (Fodrin beta chain) |
| Q01201 | 1 | Transcription factor RelB (I-Rel) |
| Q01955 | 1 | Collagen alpha 3(IV) chain precursor (Goodpasture antigen) |
| Q01970 | 1 | 1-phosphatidylinositol-4,5-bisphosphate phosphodiesterase beta 3 (EC 3.1.4.11) (Phosphoinositide phospholipase C) (PLC-beta-3) (Phospholipase C-beta-3) |
| Q01974 | 1 | Tyrosine-protein kinase transmembrane receptor ROR2 precursor (EC 2.7.1.112) (Neurotrophic tyrosine kinase, receptor-related 2) |
| Q02246 | 1 | Contactin 2 precursor (Axonin-1) (Axonal glycoprotein TAG-1) (Transient axonal glycoprotein 1) (TAX-1) |
| Q02646 | 1 | MBP-2 (MHC Binding Protein-2) |
| Q04637 | 1 | Eukaryotic translation initiation factor 4 gamma 1 (eIF-4-gamma 1) (eIF-4G1) (eIF-4G) (p220) |
| Q04695 | 1 | Keratin, type I cytoskeletal 17 (Cytokeratin 17) (K17) (CK 17) (39.1) |
| Q04771 | 1 | Activin receptor type I precursor (EC 2.7.1.37) (ACTR-I) (Serine/threonine-protein kinase receptor R1) (SKR1) (Activin receptor-like kinase 2) (ALK-2) (TGF-B superfamily receptor type I) (TSR-I) |
| Q04917 | 1 | 14-3-3 protein eta (Protein AS1) |
| Q05708 | 1 | Undulin 2 (Fragment) |
| Q06830 | 1 | Peroxiredoxin 1 (EC 1.11.1.—) (Thioredoxin peroxidase 2) (Thioredoxin-dependent peroxide reductase 2) (Proliferation-associated protein PAG) (Natural killer cell enhancing factor A) (NKEF-A) |
| Q07507 | 1 | Dermatopontin precursor (Tyrosine-rich acidic matrix protein) (TRAMP) |
| Q08043 | 1 | Alpha-actinin 3 (Alpha actinin skeletal muscle isoform 3) (F-actin cross linking protein) |
| Q08170 | 1 | Splicing factor, arginine/serine-rich 4 (Pre-mRNA splicing factor SRP75) (SRP001LB) |
| Q10586 | 1 | D-site-binding protein (Albumin D box-binding protein) (TAXREB302) |
| Q12756 | 1 | Kinesin-like protein KIF1A (Axonal transporter of synaptic vesicles) |
| Q12809 | 1 | Potassium voltage-gated channel subfamily H member 2 (Voltage-gated potassium channel subunit Kv11.1) (Ether-a-go-go related gene potassium channel 1) (H-ERG) (Erg1) (Ether-a-go-go related protein 1) (Eag related protein 1) (eag homolog) |
| Q12815 | 1 | Trophinin-associated protein (Tastin) (Trophinin-assisting protein) |
| Q12891 | 1 | Hyaluronidase 2 precursor (EC 3.2.1.35) (Hyal-2) (Hyaluronoglucosaminidase 2) (LUCA-2) |
| Q12931 | 1 | Heat shock protein 75 kDa, mitochondrial precursor (HSP 75) (Tumor necrosis factor type 1 receptor associated protein) (TRAP-1) (TNFR-associated protein 1) |
| Q12955 | 1 | Ankyrin 3 (ANK-3) (Ankyrin G) |
| Q12959 | 1 | Presynaptic protein SAP97 (Synapse-associated protein 97) (Discs, large homolog 1) (hDlg) |
| Q12988 | 1 | Heat-shock protein beta-3 (HspB3) (Heat shock 17 kDa protein) |
| Q13126 | 1 | S-methyl-5-thioadenosine phosphorylase (EC 2.4.2.28) (5'-methylthioadenosine phosphorylase) (MTA phosphorylase) (MTAPase) |
| Q13145 | 1 | BMP and activin membrane-bound inhibitor homolog precursor (Putative transmembrane protein NMA) (Non-metastatic gene A protein) |
| Q13214 | 1 | Semaphorin 3B precursor (Semaphorin V) (Sema V) (Sema A(V)) |
| Q13228 | 1 | Selenium-binding protein 1 |
| Q13283 | 1 | Ras-GTPase-activating protein binding protein 1 (GAP SH3-domain binding protein 1) (G3BP-1) (DNA helicase VIII) (HDH-VIII) |
| Q13330 | 1 | Metastasis-associated protein MTA1 |
| Q13393 | 1 | Phospholipase D1 (EC 3.1.4.4) (PLD 1) (Choline phosphatase 1) (Phosphatidylcholine-hydrolyzing phospholipase D1) (hPLD1) |
| Q13509 | 1 | Tubulin beta-4 chain (Tubulin beta-III) |
| Q13690 | 1 | Hypothetical protein (Fragment) |
| Q13813 | 1 | Spectrin alpha chain, brain (Spectrin, non-erythroid alpha chain) (Alpha-II spectrin) (Fodrin alpha chain) |
| Q13822 | 1 | Ectonucleotide pyrophosphatase/phosphodiesterase 2 (E-NPP 2) (Phosphodiesterase I/nucleotide pyrophosphatase 2) (Phosphodiesterase I alpha) (PD-Ialpha) (Autotaxin) [Includes: Alkaline phosphodiesterase I (EC 3.1.4.1); Nucleotide pyrophosphatase (EC 3.6.1. |
| Q13976 | 1 | cGMP-dependent protein kinase 1, alpha isozyme (EC 2.7.1.37) (CGK 1 alpha) (cGKI-alpha) |
| Q14151 | 1 | Scaffold attachment factor B2 |
| Q14166 | 1 | Hypothetical protein KIAA0153 |
| Q14191 | 1 | Werner syndrome helicase |
| Q14195 | 1 | Dihydropyrimidinase related protein-3 (DRP-3) (Unc-33-like phosphoprotein) (ULIP protein) (Collapsin response mediator protein 4) (CRMP-4) |
| Q14215 | 1 | Nebulin (Fragment) |
| Q14324 | 1 | Myosin-binding protein C, fast-type (Fast MyBP-C) (C-protein, skeletal muscle fast-isoform) |
| Q14521 | 1 | Giant larvae homologue |
| Q14526 | 1 | Hypermethylated in cancer 1 protein (Hic-1) (Zinc finger and BTB domain containing protein 29) |
| Q14624 | 1 | Inter-alpha-trypsin inhibitor heavy chain H4 precursor (ITI heavy chain H4) (Inter-alpha-inhibitor heavy chain 4) (Inter-alpha-trypsin inhibitor family heavy chain-related protein) (IHRP) (Plasma kallikrein sensitive glycoprotein 120) (PK-120) (GP120) (PR |

TABLE 1-continued

| GenBank Accession | Number of Peptide analytes | Protein |
|---|---|---|
| Q14692 | 1 | Ribosome biogenesis protein BMS1 homolog |
| Q15177 | 1 | Prepro-alpha2(I) collagen precursor |
| Q15369 | 1 | Transcription elongation factor B polypeptide 1 (RNA polymerase II transcription factor SIII subunit C) (SIII p15) (Elongin C) (EloC) (Elongin 15 kDa subunit) |
| Q15415 | 1 | YRRM2 |
| Q15631 | 1 | Translin |
| Q15699 | 1 | Cartilage homeoprotein 1 (CART-1) |
| Q15751 | 1 | P532 |
| Q15811 | 1 | Intersectin 1 (SH3 domain-containing protein 1A) (SH3P17) |
| Q15819 | 1 | Ubiquitin-conjugating enzyme E2 variant 2 (MMS2) (Enterocyte differentiation associated factor EDAF-1) (Enterocyte differentiation promoting factor) (EDPF-1) (Vitamin D3 inducible protein) (DDVit 1) |
| Q15858 | 1 | Sodium channel protein type IX alpha subunit (Voltage-gated sodium channel alpha subunit Nav1.7) (Neuroendocrine sodium channel) (hNE-Na) (Peripheral sodium channel 1) |
| Q16281 | 1 | Cyclic-nucleotide-gated cation channel alpha 3 (CNG channel alpha 3) (CNG-3) (CNG3) (Cyclic nucleotide gated channel alpha 3) (Cone photoreceptor cGMP-gated channel alpha subunit) |
| Q16352 | 1 | Alpha-internexin (Alpha-Inx) (66 kDa neurofilament protein) (Neurofilament-66) (NF-66) |
| Q16363 | 1 | Laminin alpha-4 chain precursor |
| Q16853 | 1 | Membrane copper amine oxidase (EC 1.4.3.6) (Vascular adhesion protein-1) (VAP-1) (HPAO) |
| Q5U5L5 | 1 | Jumonji, AT rich interactive domain 2 protein (OTTHUMP00000016058) |
| Q5VT98 | 1 | Novel protein similar to preferentially expressed antigen in melanoma (PRAME) (OTTHUMP00000044421) |
| Q5VU33 | 1 | Novel protein (MGC27277) (Fragment) |
| Q5VWI3 | 1 | Nebulin-related anchoring protein |
| Q5VWM4 | 1 | Novel protein similar to preferentially expressed antigen in melanoma (PRAME) |
| Q5VXX4 | 1 | Novel protein (Fragment) |
| Q5VZK9 | 1 | OTTHUMP00000039401 |
| Q64FK3 | 1 | Breast and ovarian cancer susceptibility protein 1 (Fragment) |
| Q66YK6 | 1 | Rap1 interacting factor 1 |
| Q672J1 | 1 | Multiple myeloma SET domain containing protein type III |
| Q68CS9 | 1 | Hypothetical protein DKFZp686B07186 |
| Q68DN1 | 1 | Hypothetical protein DKFZp781D2023 |
| Q68DN6 | 1 | Hypothetical protein DKFZp781D1923 |
| Q68DU2 | 1 | Hypothetical protein DKFZp781J054 |
| Q6AI43 | 1 | Hypothetical protein DKFZp781C08198 |
| Q6AWC0 | 1 | Hypothetical protein DKFZp451L187 (Fragment) |
| Q6DKQ9 | 1 | Cell division cycle 2-like 5 (Cholinesterase-related cell division controller) |
| Q6F5E8 | 1 | RGD, leucine-rich repeat, tropomodulin and proline-rich containing protein (Fragment) |
| Q6IPK3 | 1 | TNXB protein (Fragment) |
| Q6IPM5 | 1 | Hypothetical protein (Fragment) |
| Q6IPS3 | 1 | Hypothetical protein |
| Q6K0P6 | 1 | Interferon-inducible protein X beta 2 isoform (IFIX) |
| Q6P055 | 1 | Hypothetical protein |
| Q6P3X8 | 1 | PiggyBac transposable element derived 2 |
| Q6P6B5 | 1 | TAF3 protein (Fragment) |
| Q6PCB0 | 1 | Von Willebrand factor A domain-related protein, isoform 1 (WARP) |
| Q6PGP2 | 1 | Hypothetical protein |
| Q6PHR5 | 1 | FLJ21908 protein |
| Q6S376 | 1 | Plectin 11 |
| Q6SPF0 | 1 | Atherin |
| Q6URW7 | 1 | Normal early placenta (Fragment) |
| Q6UXY1 | 1 | APEM9336 |
| Q6UYC9 | 1 | Echinoderm microtubule associated protein-like 5 (Fragment) |
| Q6ZMR3 | 1 | L-lactate dehydrogenase A-like 6A (EC 1.1.1.27) |
| Q6ZMX3 | 1 | Hypothetical protein FLJ16614 |
| Q6ZN17 | 1 | Hypothetical protein FLJ16517 |
| Q6ZNE1 | 1 | Hypothetical protein FLJ16186 |
| Q6ZNP2 | 1 | Hypothetical protein FLJ27410 |
| Q6ZP65 | 1 | Hypothetical protein FLJ26450 |
| Q6ZQQ8 | 1 | Hypothetical protein FLJ46160 |
| Q6ZR27 | 1 | Hypothetical protein FLJ46705 |
| Q6ZR36 | 1 | Hypothetical protein FLJ46690 |
| Q6ZRH9 | 1 | Hypothetical protein FLJ46347 |
| Q6ZRM5 | 1 | Hypothetical protein FLJ46248 |
| Q6ZRQ5 | 1 | Hypothetical protein FLJ46180 |
| Q6ZRW7 | 1 | Hypothetical protein FLJ46024 |
| Q6ZSE9 | 1 | Hypothetical protein FLJ45584 |
| Q6ZSF8 | 1 | Hypothetical protein FLJ45563 |
| Q6ZSS2 | 1 | Hypothetical protein FLJ45248 |
| Q6ZSS4 | 1 | Hypothetical protein FLJ45244 |
| Q6ZSV6 | 1 | Hypothetical protein FLJ45178 |
| Q6ZTQ1 | 1 | Hypothetical protein FLJ44382 |

TABLE 1-continued

| GenBank Accession | Number of Peptide analytes | Protein |
|---|---|---|
| Q6ZTQ9 | 1 | Hypothetical protein FLJ44342 |
| Q6ZU99 | 1 | Hypothetical protein FLJ43880 |
| Q6ZUF5 | 1 | Hypothetical protein FLJ43756 |
| Q6ZUX1 | 1 | Hypothetical protein FLJ43252 |
| Q6ZUY2 | 1 | Hypothetical protein FLJ43213 |
| Q6ZUZ4 | 1 | Hypothetical protein FLJ43187 |
| Q6ZVJ1 | 1 | Hypothetical protein FLJ42519 |
| Q6ZVW2 | 1 | Hypothetical protein FLJ42006 |
| Q71U36 | 1 | Tubulin alpha-3 chain (Alpha-tubulin 3) (Tubulin B-alpha-1) |
| Q76B58 | 1 | DBCCR1-like (OTTHUMP00000060752) (DBCCR1L) |
| Q7L5L3 | 1 | MGC4171 protein |
| Q7LBC6 | 1 | Nuclear protein 5qNCA |
| Q7M4L6 | 1 | Shb-like adapter protein, Shf |
| Q7RTY9 | 1 | Testis serine protease 1 precursor |
| Q7Z2I9 | 1 | ATP-binding cassette sub-family A member 10 |
| Q7Z3Y8 | 1 | Type I inner root sheath specific keratin 25 irs3 |
| Q7Z527 | 1 | GMP dehydrogenase |
| Q7Z5L5 | 1 | Alpha 1 type XXIV collagen precursor |
| Q7Z645 | 1 | Collagen, type VI, alpha 1, |
| Q7Z659 | 1 | Hypothetical protein DKFZp779H0156 (Fragment) |
| Q7Z7G1 | 1 | MIST |
| Q86SF2 | 1 | N-acetylgalactosaminyltransferase 7 (EC 2.4.1.—) (Protein-UDP acetylgalactosaminyltransferase 7) (UDP-GalNAc:polypeptide N-acetylgalactosaminyltransferase 7) (Polypeptide GalNAc transferase 7) (GalNAc-T7) (pp-GaNTase 7) |
| Q86SM7 | 1 | G protein-coupled receptor PGR4 (Fragment) |
| Q86T65 | 1 | Disheveled associated activator of morphogenesis 2 |
| Q86TS5 | 1 | Full-length cDNA 5-PRIME end of clone CS0DF013YM24 of Fetal brain of Homo sapiens (human) (Fragment) |
| Q86U06 | 1 | RNA-binding region containing protein 4 (Splicing factor SF2) (PP239) |
| Q86UE3 | 1 | Zinc finger protein 546 |
| Q86UQ4 | 1 | ABC A13 |
| Q86VV8 | 1 | RTTN protein (Fragment) |
| Q86W64 | 1 | TPM1 protein (Fragment) |
| Q86WE1 | 1 | Sarcoma antigen NY-SAR-97 (Fragment) |
| Q86X24 | 1 | HORMA domain containing protein (Novel protein) (DKFZp434A1315) |
| Q86XP3 | 1 | RNA helicase-related protein |
| Q86Y13 | 1 | Ubiquitin ligase protein DZIP3 (EC 6.3.2.—) (DAZ-interacting protein 3) (RNA-binding ubiquitin ligase of 138 kDa) (hRUL138) |
| Q86YB8 | 1 | ERO1-like protein beta precursor (EC 1.8.4.—) (ERO1-Lbeta) (Oxidoreductin 1-1beta) (Endoplasmic oxidoreductin 1-like protein B) |
| Q8IUS5 | 1 | Abhydrolase domain containing 7 |
| Q8IVL0 | 1 | Steerin3 protein |
| Q8IVP0 | 1 | MGC27277 protein |
| Q8IVR4 | 1 | COL23A1 protein |
| Q8IXE5 | 1 | Seven transmembrane helix receptor |
| Q8IY17 | 1 | Neuropathy target esterase (Fragment) |
| Q8IY92 | 1 | BTB/POZ domain containing protein 12 |
| Q8IYR0 | 1 | Protein C6orf165 |
| Q8IZC6 | 1 | Collagen XXVII proalpha 1 chain precursor (OTTHUMP00000021970) |
| Q8IZQ1 | 1 | ALFY |
| Q8J028 | 1 | Ovarian zinc finger protein |
| Q8N3A8 | 1 | Hypothetical protein DKFZp762K2011 |
| Q8N3E6 | 1 | Hypothetical protein DKFZp761L1023 (Fragment) |
| Q8N4S0 | 1 | Hypothetical protein FLJ23518 |
| Q8N590 | 1 | Polymerase (DNA directed) iota |
| Q8N7Z2 | 1 | Hypothetical protein FLJ40198 |
| Q8N838 | 1 | Hypothetical protein FLJ40083 |
| Q8N9J2 | 1 | Hypothetical protein FLJ37051 |
| Q8NAG3 | 1 | Hypothetical protein FLJ35393 |
| Q8NAN2 | 1 | Hypothetical protein FLJ35093 (Hypothetical protein DKFZp686M07166) |
| Q8NAZ4 | 1 | Hypothetical protein FLJ34483 |
| Q8NB92 | 1 | Hypothetical protein FLJ34056 |
| Q8NBZ3 | 1 | Hypothetical protein FLJ90646 |
| Q8NC60 | 1 | Hypothetical protein FLJ90472 |
| Q8NC68 | 1 | Hypothetical protein FLJ90455 |
| Q8NDC7 | 1 | Hypothetical protein DKFZp547B0614 (Fragment) |
| Q8NDG7 | 1 | Hypothetical protein DKFZp434N1720 (Fragment) |
| Q8NE71 | 1 | ATP-binding cassette, sub-family F, member 1 (ATP-binding cassette 50) (TNF-alpha stimulated ABC protein) |
| Q8NEK9 | 1 | Chromosome 1 open reading frame 26 |
| Q8NEZ4 | 1 | Myeloid/lymphoid or mixed-lineage leukemia protein 3 homolog (Histone-lysine N-methyltransferase, H3 lysine-4 specific MLL3) (EC 2.1.1.43) (Homologous to ALR protein) |

TABLE 1-continued

| GenBank Accession | Number of Peptide analytes | Protein |
|---|---|---|
| Q8NEZ9 | 1 | FLJ00406 protein (Fragment) |
| Q8NF91 | 1 | Nesprin 1 (Nuclear envelope spectrin repeat protein 1) (Synaptic nuclear envelope protein 1) (Syne-1) (Myocyte nuclear envelope protein 1) (Myne-1) (Enaptin) |
| Q8NFA0 | 1 | Ubiquitin carboxyl-terminal hydrolase 32 (EC 3.1.2.15) (Ubiquitin thiolesterase 32) (Ubiquitin-specific processing protease 32) (Deubiquitinating enzyme 32) (NY-REN-60 antigen) |
| Q8NFJ9 | 1 | Bardet-Biedl syndrome 1 protein (BBS2-like protein 2) |
| Q8NFP9 | 1 | Neurobeachin protein (Lysosomal trafficking regulator 2) (BCL8B protein) |
| Q8NHQ8 | 1 | Protein C12orf2 (Carcinoma associated protein HOJ-1) |
| Q8NHZ8 | 1 | CDC26 subunit of anaphase promoting complex (Cell division cycle 26) |
| Q8TB03 | 1 | Chromosome X open reading frame 38 |
| Q8TCT7 | 1 | Signal peptide peptidase-like 2B (EC 3.4.99.—) (SPP-like 2B protein) (SPPL2b protein) (Intramembrane protease 4) (IMP4) (Presenilin-like protein 1) |
| Q8TDC3 | 1 | Probable serine/threonine-protein kinase KIAA1811 (EC 2.7.1.37) |
| Q8TDH8 | 1 | Citrate lyase beta subunit (Citrate lyase beta like) |
| Q8TDP0 | 1 | Apical protein 2 |
| Q8TDT7 | 1 | Putative G-protein coupled receptor |
| Q8TDX9 | 1 | Polycystic kidney disease 1-like 1 protein (Polycystin 1L1) |
| Q8TEE6 | 1 | FLJ00251 protein (Fragment) |
| Q8TEM4 | 1 | FLJ00169 protein (Fragment) |
| Q8TEM6 | 1 | FLJ00167 protein (Fragment) |
| Q8TER5 | 1 | FLJ00128 protein (Fragment) |
| Q8TEY7 | 1 | Ubiquitin carboxyl-terminal hydrolase 33 (EC 3.1.2.15) (Ubiquitin thiolesterase 33) (Ubiquitin-specific processing protease 33) (Deubiquitinating enzyme 33) (VHL-interacting deubiquitinating enzyme 1) |
| Q8TF19 | 1 | KIAA1983 protein (Fragment) |
| Q8TF45 | 1 | Zinc finger protein 418 |
| Q8WTS1 | 1 | CGI58 protein |
| Q8WWI1 | 1 | LIM domain only protein 7 (LOMP) (F-box only protein 20) |
| Q8WWM7 | 1 | Ataxin-2-like protein (Ataxin-2 domain protein) (Ataxin-2 related protein) |
| Q8WXD9 | 1 | Cask-interacting protein 1 |
| Q8WXE9 | 1 | Stonin 2 (Stoned B) |
| Q8WYY1 | 1 | Hypothetical protein |
| Q92889 | 1 | DNA repair endonuclease XPF (EC 3.1.—.—) (DNA excision repair protein ERCC-4) (DNA-repair protein complementing XP-F cell) (Xeroderma pigmentosum group F complementing protein) |
| Q92994 | 1 | Transcription factor IIIB 90 kDa subunit (TFIIIB90) (hTFIIIB90) (B-related factor 1) (hBRF) (TATA box-binding protein-associated factor, RNA polymerase III, subunit 2) (TAF3B2) |
| Q93038 | 1 | Tumor necrosis factor receptor superfamily member 25 precursor (WSL-1 protein) (Apoptosis-mediating receptor DR3) (Apoptosis-mediating receptor TRAMP) (Death domain receptor 3) (WSL protein) (Apoptosis inducing receptor AIR) (Apo-3) (Lymphocyte associated) |
| Q969G5 | 1 | HSRBC protein (Protein kinase C, delta binding protein) |
| Q96AC1 | 1 | Pleckstrin homology domain containing family C member 1 (Kindlin 2) (Mitogen-inducible gene 2 protein) (Mig-2) |
| Q96B86 | 1 | Repulsive guidance molecule A precursor (RGM domain family member A) |
| Q96B97 | 1 | SH3-domain kinase binding protein 1 (Cbl-interacting protein of 85 kDa) (Human Src-family kinase binding protein 1) (HSB-1) (CD2 binding protein 3) (CD2BP3) |
| Q96BE2 | 1 | MYO1G protein (Fragment) |
| Q96BP2 | 1 | Coiled-coil-helix-coiled-coil-helix domain containing 1 |
| Q96BV3 | 1 | NT5C2L1 protein |
| Q96CG5 | 1 | Hypothetical protein (Fragment) |
| Q96CX2 | 1 | Potassium channel tetramerisation domain containing protein 12 (Pfetin) (Predominantly fetal expressed T1 domain) |
| Q96DJ8 | 1 | Hypothetical protein FLJ25312 |
| Q96DN4 | 1 | Hypothetical protein FLJ31897 |
| Q96DV1 | 1 | Myosin light chain kinase (MLCK) |
| Q96FR0 | 1 | PLEKHA6 protein |
| Q96FU4 | 1 | Hypothetical protein |
| Q96GQ7 | 1 | Probable ATP-dependent RNA helicase DDX27 (DEAD-box protein 27) (HSPC259) (PP3241) |
| Q96HY7 | 1 | Dehydrogenase E1 and transketolase domain containing protein 1 |
| Q96I51 | 1 | Williams-Beuren syndrome chromosome region 16 protein |
| Q96IU4 | 1 | CCG1-interacting factor B |
| Q96JF9 | 1 | KIAA1868 protein (Fragment) |
| Q96JK4 | 1 | KIAA1822 protein (Fragment) |
| Q96JM2 | 1 | Zinc finger protein 462 |
| Q96JX8 | 1 | Hypothetical protein FLJ14909 |
| Q96K26 | 1 | Hypothetical protein FLJ14834 |
| Q96L12 | 1 | Calreticulin 3 precursor (Calreticulin 2) |
| Q96L34 | 1 | MAP/microtubule affinity-regulating kinase 4 (EC 2.7.1.37) (MAP/microtubule affinity-regulating kinase like 1) |
| Q96L96 | 1 | Muscle alpha-kinase |
| Q96LM3 | 1 | Hypothetical protein FLJ25373 |

TABLE 1-continued

| GenBank Accession | Number of Peptide analytes | Protein |
|---|---|---|
| Q96MB5 | 1 | Hypothetical protein FLJ32682 |
| Q96MC7 | 1 | Hypothetical protein FLJ32603 |
| Q96ML4 | 1 | Hypothetical protein FLJ32194 |
| Q96MN5 | 1 | Hypothetical protein FLJ32112 (Novel protein) |
| Q96NY2 | 1 | DEAD/DEXH helicase DDX31 (OTTHUMP00000064614) |
| Q96P94 | 1 | Dermatan-4-sulfotransferase-1 (Dermatan 4-sulfotransferase) |
| Q96PX5 | 1 | KIAA1913 protein (Fragment) |
| Q96RK0 | 1 | Capicua protein |
| Q96RR4 | 1 | Calcium/calmodulin-dependent protein kinase kinase 2 (EC 2.7.1.37) (Calcium/calmodulin-dependent protein kinase kinase beta) (CaM-kinase kinase beta) (CaM-KK beta) (CaMKK beta) |
| Q96S08 | 1 | Some homology with holliday junction DNA helicase RUVB like |
| Q96S66 | 1 | Mid-1-related chloride channel 1 (Hypothetical protein KIAA0761) (MCLC) |
| Q96T58 | 1 | Msx2-interacting protein (SMART/HDAC1 associated repressor protein) |
| Q96TA2 | 1 | ATP-dependent metalloprotease YME1L1 (EC 3.4.24.—) (YME1-like protein 1) (ATP-dependent metalloprotease FtsH1) (Meg-4) (Presenilin-associated metalloprotease) (PAMP) (UNQ1868/PRO4304) |
| Q99457 | 1 | Nucleosome assembly protein 1-like 3 |
| Q99460 | 1 | 26S proteasome non-ATPase regulatory subunit 1 (26S proteasome regulatory subunit RPN2) (26S proteasome regulatory subunit S1) (26S proteasome subunit p112) |
| Q99623 | 1 | B-cell receptor-associated protein BAP37 (Repressor of estrogen receptor activity) (D-prohibitin) |
| Q99715 | 1 | Collagen alpha 1(XII) chain precursor |
| Q99718 | 1 | ESE-1a |
| Q99727 | 1 | Metalloproteinase inhibitor 4 precursor (TIMP-4) (Tissue inhibitor of metalloproteinases-4) |
| Q99798 | 1 | Aconitate hydratase, mitochondrial precursor (EC 4.2.1.3) (Citrate hydro-lyase) (Aconitase) |
| Q99814 | 1 | Endothelial PAS domain protein 1 (EPAS-1) (Member of PAS protein 2) (MOP2) (Hypoxia-inducible factor 2 alpha) (HIF-2 alpha) (HIF2 alpha) (HIF-1 alpha-like factor) (HLF) |
| Q99996 | 1 | A-kinase anchor protein 9 (Protein kinase A anchoring protein 9) (PRKA9) (A-kinase anchor protein 450 kDa) (AKAP 450) (A-kinase anchor protein 350 kDa) (AKAP 350) (hgAKAP 350) (AKAP 120 like protein) (Hyperion protein) (Yotiao protein) (Centrosome- and Go |
| Q9BS17 | 1 | LRRIQ1 protein |
| Q9BS33 | 1 | FLJ11218 protein |
| Q9BSE5 | 1 | Agmatinase, mitochondrial precursor (EC 3.5.3.11) (Agmatine ureohydrolase) (AUH) |
| Q9BSG0 | 1 | Protease-associated domain-containing protein of 21 kDa precursor (hPAP21) (UNQ833/PRO1760) |
| Q9BU70 | 1 | Chromosome 9 open reading frame 156 |
| Q9BUN0 | 1 | DEAD/H (Asp-Glu-Ala-Asp/His) box polypeptide 32 (Fragment) |
| Q9BUP0 | 1 | EF-hand domain-containing protein 1 (Swiprosin 2) (PP3051) |
| Q9BUR4 | 1 | FLJ10385 protein |
| Q9BUY9 | 1 | Growth arrest-specific 2 like 1, isoform a |
| Q9BVC6 | 1 | Hypothetical protein MGC5508 |
| Q9BVP4 | 1 | PDLIM3 protein (Alpha-actinin-2-associated LIM protein) |
| Q9BX44 | 1 | BA92K2.2 (Similar to ubiquitin) |
| Q9BXG4 | 1 | Spermatid perinuclear RNA-binding protein |
| Q9BYX7 | 1 | FKSG30 |
| Q9C0A8 | 1 | KIAA1755 protein (Fragment) |
| Q9C0D3 | 1 | KIAA1730 protein (Fragment) |
| Q9C0E5 | 1 | KIAA1718 protein (Fragment) |
| Q9C0J8 | 1 | WD-repeat protein 33 (WD-repeat protein WDC146) |
| Q9GZM7 | 1 | Tubulointerstitial nephritis antigen-related protein precursor (Glucocorticoid-inducible protein) (Oxidized-LDL responsive gene 2) (Hypothetical protein PSEC0088) (LCN7) (P3ECSL) |
| Q9GZN0 | 1 | Striatum-specific G potein-coupled receptor (Striatum-specific G protein-coupled receptor) |
| Q9GZY0 | 1 | Nuclear RNA export factor 2 (TAP-like protein 2) (TAPL-2) |
| Q9H0V1 | 1 | Hypothetical protein DKFZp564C012 |
| Q9H1I7 | 1 | Calcineurin-binding protein calsarcin-2 |
| Q9H1I8 | 1 | Activating signal cointegrator 1 complex subunit 2 (ASC-1 complex subunit p100) (Trip4 complex subunit p100) |
| Q9H280 | 1 | Serologically defined breast cancer antigen NY-BR-62 (Fragment) |
| Q9H297 | 1 | Sarcolemmal associated protein 1 |
| Q9H2G2 | 1 | CTCL tumor antigen se20-9 (Ste20-related serine\threonine kinase) (SLK) |
| Q9H2K2 | 1 | Tankyrase 2 (EC 2.4.2.30) (TANK2) (TNKS-2) (TRF1-interacting ankyrin-related ADP-ribose polymerase 2) (Tankyrase-like protein) (Tankyrase-related protein) |
| Q9H2T7 | 1 | Ran-binding protein 17 |
| Q9H3E2 | 1 | Sorting nexin 25 (MSTP043) |
| Q9H3P9 | 1 | MCM10 homolog (MCM10 minichromosome maintenance deficient 10) (*S. cerevisiae*) (OTTHUMP00000045155) |
| Q9H4A3 | 1 | Serine/threonine-protein kinase WNK1 (EC 2.7.1.37) (Protein kinase with no lysine 1) (Protein kinase, lysine-deficient 1) (Kinase deficient protein) |

TABLE 1-continued

| GenBank Accession | Number of Peptide analytes | Protein |
|---|---|---|
| Q9H4B4 | 1 | Serine/threonine-protein kinase PLK3 (EC 2.7.1.37) (Polo-like kinase 3) (PLK-3) (Cytokine-inducible serine/threonine-protein kinase) (FGF-inducible kinase) (Proliferation-related kinase) |
| Q9H4B6 | 1 | Salvador homolog 1 protein (45 kDa WW domain protein) (hWW45) |
| Q9H4E5 | 1 | Rho-related GTP-binding protein RhoJ (Tc10-like GTP-binding protein TCL) |
| Q9H4Q3 | 1 | PR-domain zinc finger protein 13 |
| Q9H5C5 | 1 | Hypothetical protein FLJ23584 |
| Q9H6Y5 | 1 | Hypothetical protein FLJ21687 |
| Q9H6Z0 | 1 | Hypothetical protein FLJ21665 (Tubulin, alpha-like 3) |
| Q9H799 | 1 | Hypothetical protein FLJ21126 |
| Q9H7T0 | 1 | Hypothetical protein FLJ14298 |
| Q9H897 | 1 | Hypothetical protein FLJ13848 |
| Q9H8G1 | 1 | Zinc finger protein 430 |
| Q9H9D7 | 1 | Hypothetical protein FLJ12822 |
| Q9H9I3 | 1 | Hypothetical protein FLJ12730 |
| Q9HBX6 | 1 | Phosphoinositide-specific phospholipase C PLC-epsilon |
| Q9HCC0 | 1 | Methylcrotonyl-CoA carboxylase beta chain, mitochondrial precursor (EC 6.4.1.4) (3-Methylcrotonyl-CoA carboxylase 2) (MCCase beta subunit) (3-methylcrotonyl-CoA:carbon dioxide ligase beta subunit) |
| Q9HCC9 | 1 | Zinc finger FYVE domain containing protein 28 |
| Q9HCL2 | 1 | Glycerol-3-phosphate acyltransferase, mitochondrial precursor (EC 2.3.1.15) (GPAT) |
| Q9NPD8 | 1 | Ubiquitin-conjugating enzyme isolog (HSPC150 protein similar to ubiquitin-conjugating enzyme) (Hypothetical protein FLJ20497) (OTTHUMP00000060941) (Ubiquitin-conjugating enzyme E2) |
| Q9NQZ8 | 1 | Endothelial zinc finger protein induced by tumor necrosis factor alpha (Zinc finger protein 71) (ZNF47) |
| Q9NR22 | 1 | Protein arginine N-methyltransferase 4 (EC 2.1.1.—) (Heterogeneous nuclear ribonucleoprotein methyltransferase-like protein 4) |
| Q9NRA8 | 1 | Eukaryotic translation initiation factor 4E transporter (eIF4E transporter) (4E-T) (Eukaryotic translation initiation factor 4E nuclear import factor 1) |
| Q9NTK5 | 1 | Putative GTP-binding protein PTD004 (PRO2455) |
| Q9NTZ6 | 1 | RNA-binding protein 12 (RNA binding motif protein 12) (SH3/WW domain anchor protein in the nucleus) (SWAN) (HRIHFB2091) |
| Q9NVD7 | 1 | Alpha-parvin (Calponin-like integrin-linked kinase binding protein) (CH-ILKBP) |
| Q9NVR0 | 1 | Hypothetical protein FLJ10572 (Hypothetical protein KLHL11) |
| Q9NX06 | 1 | Hypothetical protein FLJ20505 |
| Q9NXX3 | 1 | Hypothetical protein FLJ20006 |
| Q9NYC9 | 1 | Ciliary dynein heavy chain 9 (Axonemal beta dynein heavy chain 9) |
| Q9NZI8 | 1 | MRNA-binding protein CRDBP |
| Q9NZQ8 | 1 | MTR1 |
| Q9P150 | 1 | PRO2760 |
| Q9P188 | 1 | Hypothetical protein PRO1866 |
| Q9P242 | 1 | KIAA1486 protein (Fragment) |
| Q9P286 | 1 | Serine/threonine-protein kinase PAK 7 (EC 2.7.1.37) (p21-activated kinase 7) (PAK-7) (PAK-5) |
| Q9P2A8 | 1 | KIAA1440 protein (Fragment) |
| Q9P2D1 | 1 | Chromodomain-helicase-DNA-binding protein 7 (CHD-7) (Fragment) |
| Q9P2D5 | 1 | KIAA1412 protein (Fragment) |
| Q9P2E3 | 1 | Protein KIAA1404 |
| Q9P2F9 | 1 | Zinc finger protein 319 |
| Q9P2J2 | 1 | KIAA1355 protein (Fragment) |
| Q9UBG7 | 1 | Recombining binding protein suppressor of hairless-like protein (Transcription factor RBP-L) |
| Q9UBI6 | 1 | Guanine nucleotide-binding protein G(I)/G(S)/G(O) gamma-12 subunit |
| Q9UBM7 | 1 | 7-dehydrocholesterol reductase (EC 1.3.1.21) (7-DHC reductase) (Sterol delta-7-reductase) (Putative sterol reductase SR-2) |
| Q9UF55 | 1 | Hypothetical protein DKFZp434A2017 (Fragment) |
| Q9UHK6 | 1 | Alpha-methylacyl-CoA racemase (EC 5.1.99.4) (2-methylacyl-CoA racemase) |
| Q9UIF9 | 1 | Bromodomain adjacent to zinc finger domain 2A (Transcription termination factor-I interacting protein 5) (TTF-I interacting protein 5) (Tip5) (hWALp3) |
| Q9UII5 | 1 | Zinc finger protein ZFD25 |
| Q9UJQ7 | 1 | Protein C20orf79 |
| Q9UJY4 | 1 | ADP-ribosylation factor binding protein GGA2 (Golgi-localized, gamma ear-containing, ARF-binding protein 2) (Gamma-adaptin related protein 2) (Vear) (VHS domain and ear domain of gamma-adaptin) |
| Q9UK17 | 1 | Potassium voltage-gated channel subfamily D member 3 (Voltage-gated potassium channel subunit Kv4.3) |
| Q9UKG9 | 1 | Peroxisomal carnitine O-octanoyltransferase (EC 2.3.1.137) (COT) |
| Q9UKP3 | 1 | Integrin beta-1 binding protein 2 (Melusin) (MSTP015) |
| Q9UKS6 | 1 | Protein kinase C and casein kinase substrate in neurons protein 3 (SH3 domain-containing protein 6511) (Endophilin I) |
| Q9UL01 | 1 | Squamous cell carcinoma antigen recognized by T cells 2 (SART2 protein) |
| Q9UL36 | 1 | Zinc finger protein 236 |
| Q9ULH9 | 1 | KIAA1241 protein (Fragment) |
| Q9ULM0 | 1 | KIAA1200 protein (Fragment) |

TABLE 1-continued

| GenBank Accession | Number of Peptide analytes | Protein |
|---|---|---|
| Q9ULN1 | 1 | KIAA1189 protein (Fragment) |
| Q9ULT4 | 1 | KIAA1135 protein (Fragment) |
| Q9ULU4 | 1 | Protein kinase C binding protein 1 (Rack7) (Cutaneous T-cell lymphoma associated antigen se14-3) (CTCL tumor antigen se14-3) (Zinc finger MYND domain containing protein 8) |
| Q9UMN6 | 1 | Myeloid/lymphoid or mixed-lineage leukemia protein 4 (Trithorax homolog 2) |
| Q9UPY5 | 1 | Cystine/glutamate transporter (Amino acid transport system xc-) (xCT) (Calcium channel blocker resistance protein CCBR1) |
| Q9UQ13 | 1 | Leucine-rich repeat protein SHOC-2 (Ras-binding protein Sur-8) |
| Q9UQ88 | 1 | PITSLRE serine/threonine-protein kinase CDC2L2 (EC 2.7.1.37) (Galactosyltransferase associated protein kinase p58/GTA) (Cell division cycle 2-like 2) (CDK11) |
| Q9Y230 | 1 | RuvB-like 2 (EC 3.6.1.—) (48-kDa TATA box-binding protein-interacting protein) (48-kDa TBP-interacting protein) (TIP49b) (Repressing pontin 52) (Reptin 52) (51 kDa erythrocyte cytosolic protein) (ECP-51) (TIP60-associated protein 54-beta) (TAP54-beta) (CG |
| Q9Y247 | 1 | XAP-5-like protein |
| Q9Y285 | 1 | Phenylalanyl-tRNA synthetase alpha chain (EC 6.1.1.20) (Phenylalanine--tRNA ligase alpha chain) (PheRS) (CML33) |
| Q9Y2B1 | 1 | Transmembrane protein 5 |
| Q9Y2G8 | 1 | KIAA0962 protein (Fragment) |
| Q9Y2H3 | 1 | KIAA0967 protein |
| Q9Y2L5 | 1 | TRS85 homolog |
| Q9Y315 | 1 | Putative deoxyribose-phosphate aldolase (EC 4.1.2.4) (Phosphodeoxyriboaldolase) (Deoxyriboaldolase) (DERA) (CGI-26) |
| Q9Y3A4 | 1 | Hypothetical protein CGI-96 (BK126B4.3) |
| Q9Y3E0 | 1 | UPF0198 protein CGI-141 (HDCMA39P) (UNQ432/PRO793) |
| Q9Y3E8 | 1 | CGI-150 protein |
| Q9Y3Q0 | 1 | N-acetylated-alpha-linked acidic dipeptidase II (EC 3.4.17.21) (NAALADase II) |
| Q9Y4Z3 | 1 | ZASP protein (Fragment) |
| Q9Y5G1 | 1 | Protocadherin gamma B3 precursor (PCDH-gamma-B3) |
| Q9Y5H1 | 1 | Protocadherin gamma A2 precursor (PCDH-gamma-A2) |
| Q9Y5Q3 | 1 | Transcription factor MafB (V-maf musculoaponeurotic fibrosarcoma oncogene homolog B) |
| Q9Y632 | 1 | APC2 protein (Fragment) |
| Q9Y679 | 1 | Ancient ubiquitous protein 1 precursor |
| Q9Y6C2 | 1 | EMILIN 1 precursor (Elastin microfibril interface-located protein 1) (Elastin microfibril interfacer 1) |
| Q9Y6D6 | 1 | Brefeldin A-inhibited guanine nucleotide-exchange protein 1 (Brefeldin A-inhibited GEP 1) (p200 ARF-GEP1) (p200 ARF guanine nucleotide exchange factor) |
| Q9Y6H8 | 1 | Gap junction alpha-3 protein (Connexin 46) (Cx46) |
| Q9Y6N5 | 1 | Sulfide:quinone oxidoreductase, mitochondrial precursor (EC 1.—.—.—) (CGI-44) |
| Q9Y6X9 | 1 | Zinc finger CW-type coiled-coil domain protein 1 |
| Q9Y6Y9 | 1 | Lymphocyte antigen 96 precursor (MD-2 protein) (ESOP-1) |

What is claimed is:

1. A method of analyzing a tissue proteome for the presence of one or more proteins comprising the steps of:
   (a) contacting a first histopathologically processed biological sample with a first buffer solution and a second histopathologically processed biological sample with a second buffer solution;
   (b) heating said first histopathologically processed biological sample and second histopathologically processed biological sample at a temperature and for a time sufficient to substantially reduce the protein cross-links present in the biological samples to form heated first and second samples;
   (c) treating the heated first and second samples with an effective amount of one or more proteolytic enzymes for a time sufficient to substantially reduce the proteins to individual peptides;
   (d) following treatment with said one or more proteolytic enzymes, separating the heated first sample using a first separation system and separating the heated second sample using a second separation system, wherein the first separation system and the second separation system comprise a chromatography matrix, thereby producing fractions of said first sample and fractions of said second sample; and
   (e) detecting the presence of at least one protein analyte from Table 1 by the presence of one or more individual peptide(s) produced by the action of said one or more proteolytic enzymes in said fractions of said first sample and said fractions of said second sample,
   thereby analyzing a tissue proteome.

2. The method of claim 1, comprising detecting more than one protein analyte from Table 1.

3. The method of claim 2, wherein said one or more proteins comprise HEF-like protein and Wnt-9a protein precursor (Wnt-14).

4. The method of claim 3, wherein said one or more proteins further comprises G protein-coupled receptor PGR4 (Fragment) and/or protein C12 or f2 (Carcinoma associated protein HOJ-1).

5. The method of claim 4, wherein said one or more proteins further comprises ADAMTS-2 precursor and/or CDC26 subunit of anaphase promoting complex.

6. The method of claim 5, wherein said one or more proteins further comprises sarcoma antigen NY-SAR-97 and/or protein kinase C binding protein 1.

7. The method of claim 6, wherein said one or more proteins further comprises 14-3-3 protein eta and/or MAP/microtubule affinity-regulating kinase.

8. The method of claim 7, wherein said one or more proteins further comprises serine/threonine-protein kinase PLK3 and/or mitogen-activated protein kinase 6.

9. The method of claim 8, wherein said one or more proteins further comprises Metalloproteinase inhibitor 4 precursor (TIMP-4) and/or Metastasis-associated protein MTA 1.

10. The method of claim 9, wherein said one or more proteins further comprises Wnt-3a protein precursor and/or Polycystic kidney disease 1-like 1 protein (Polycystin 1L1).

11. The method of claim 10, wherein said one or more proteins further comprises 14-3-3 protein epsilon (14-3-3E) and/or dual specificity protein kinase TTK.

12. The method of claim 11, wherein said one or more proteins further comprises DNA repair endonuclease XPF and/or 14-3-3 protein zeta/delta.

13. The method of claim 12, wherein said one or more proteins further comprises squamous cell carcinoma antigen recognized by T cells 2 (SART2) and/or phosphatidylethanolamine-binding protein.

14. The method of claim 13, wherein said one or more proteins further comprises 14-3-3 protein gamma and/or putative G-protein coupled receptor.

15. The method of claim 14, wherein said one or more proteins further comprises breast and ovarian cancer susceptibility protein 1 and/or ephrin-B2 precursor.

16. The method of claim 15, wherein said one or more proteins further comprises heat shock protein HSP 90-alpha (HSP 86) and/or heat shock protein HSP 90-beta.

17. The method of claim 16, wherein said one or more proteins further comprises tumor necrosis factor receptor superfamily member 25 precursor and/or prostate specific antigen precursor.

18. The method of claim 2, wherein said detecting is conducted by mass spectrometry.

19. The method of claim 1, wherein one or more nucleic acids and/or peptides present in fractions of said first sample and fractions of said second sample are immobilized on a support surface prior to said detecting.

20. The method of claims 19, wherein said detecting is accomplished by secondary antibodies, mass spectrometry, surface plasmon resonance, or atomic force microscopy.

21. The method of claim 1, wherein said detecting the presence of at least one protein analyte comprises a step of: mass spectrometry, column chromatography, protein array analysis, Western blotting, immunoprecipitation, affinity column chromatography, binding of labeled probes to a microarray, one-dimensional polyacrylamide gel electrophoresis, two-dimensional polyacrylamide gel electrophoresis, HPLC, FPLC, liquid chromatography, ELISA assays, or protein sequencing.

22. The method of claim 1 further comprising detecting one or more nucleic acids in said first histopathologically processed biological sample and said second histopathologically processed biological sample.

23. The method of claim 22, wherein said detecting one or more nucleic acids comprises a step of: mass spectrometry, column chromatography, affinity column chromatography, nucleic acid amplification, PCR, LCR, T7-based RNA amplification, binding of labeled probes to a microarray, RFLP analysis, Southern blotting, one-dimensional polyacrylamide gel electrophoresis, two-dimensional polyacrylamide gel electrophoresis, serial analysis of gene expression (SAGE), HPLC, FPLC, liquid chromatography, quantitative RT-PCR, Single Nucleotide Polymorphism detection, or nucleic acid sequencing.

* * * * *